US012758416B2

(12) United States Patent
Goff et al.

(10) Patent No.: US 12,758,416 B2
(45) Date of Patent: *Oct. 13, 2026

(54) POSITIONAL OBSTRUCTIVE SLEEP APNEA DETECTION SYSTEM

(71) Applicant: Oura Health Oy, Oulu (FI)

(72) Inventors: Thomas G. Goff, Mountain View, CA (US); Kirby Chiang, Mountain View, CA (US); Nathaniel L. Bowditch, Menlo Park, CA (US)

(73) Assignee: Oura Health Oy, Oulu (FI)

( * ) Notice: Subject to any disclaimer, the term of this patent is extended or adjusted under 35 U.S.C. 154(b) by 377 days.

This patent is subject to a terminal disclaimer.

(21) Appl. No.: 18/136,720

(22) Filed: Apr. 19, 2023

(65) Prior Publication Data

US 2023/0270586 A1 Aug. 31, 2023

Related U.S. Application Data

(63) Continuation of application No. 16/775,121, filed on Jan. 28, 2020, now Pat. No. 11,660,228, which is a (Continued)

(51) Int. Cl.

*A61B 5/1455* (2006.01)
*A61B 5/00* (2006.01)

(Continued)

(52) U.S. Cl.

CPC .............. *A61F 5/56* (2013.01); *A61B 5/0205* (2013.01); *A61B 5/0873* (2013.01); *A61B 5/11* (2013.01);

(Continued)

(58) Field of Classification Search

CPC .............. A61B 5/1455; A61B 5/14552; A61B 5/68335

See application file for complete search history.

(56) References Cited

U.S. PATENT DOCUMENTS 3,649,964 A 3/1972 Schoelz et al.
3,721,233 A 3/1973 Montgomery et al.

(Continued)

FOREIGN PATENT DOCUMENTS

CN 101678220 A 3/2010
CN 102743246 A 10/2012

(Continued)

OTHER PUBLICATIONS

Cartwright: Effect of sleep position on sleep apnea severity; Sleep; 7(2); pp. 110-114; Jun. 1984.

(Continued)

*Primary Examiner* — Marjan Fardanesh

(74) *Attorney, Agent, or Firm* — ArentFox Schiff LLP

(57) ABSTRACT

An obstructive sleep apnea detection device including an optical engagement surface adapted to engage a user's skin; a light source adapted to emit light from the optical engagement surface; a photodetector adapted to detect light at the optical engagement surface and to generate a detected light signal; a position sensor adapted to determine patient sleeping position; a controller adapted to determine and record in memory blood oxygen saturation values computed from the detected light signal and user position information from the position sensor; and a housing supporting the optical engagement surface, the photodetector, the light source, the position sensor, and the controller.

20 Claims, 17 Drawing Sheets

Related U.S. Application Data continuation of application No. 16/195,624, filed on Nov. 19, 2018, now Pat. No. 10,632,009, which is a continuation of application No. PCT/US2017/033563, filed on May 19, 2017.

(60) Provisional application No. 62/338,920, filed on May 19, 2016.

(51) Int. Cl.

| | |
|---|---|
| ***A61B 5/0205*** | (2006.01) |
| ***A61B 5/087*** | (2006.01) |
| ***A61B 5/11*** | (2006.01) |
| ***A61F 5/56*** | (2006.01) |
| *A61B 5/01* | (2006.01) |
| *A61B 5/024* | (2006.01) |
| *A61B 5/026* | (2006.01) |
| *A61B 5/113* | (2006.01) |
| *A61M 16/06* | (2006.01) |
| *A61M 16/10* | (2006.01) |

(52) U.S. Cl.

CPC ........ *A61B 5/1455* (2013.01); *A61B 5/14552* (2013.01); *A61B 5/4818* (2013.01); *A61B 5/6814* (2013.01); *A61B 5/68335* (2017.08); *A61B 5/0064* (2013.01); *A61B 5/01* (2013.01); *A61B 5/02416* (2013.01); *A61B 5/0261* (2013.01); *A61B 5/1135* (2013.01); *A61B 5/6816* (2013.01); *A61B 5/6817* (2013.01); *A61B 5/6819* (2013.01); *A61B 5/6898* (2013.01); *A61B 2560/0412* (2013.01); *A61B 2562/0219* (2013.01); *A61M 16/06* (2013.01); *A61M 16/105* (2013.01); *A61M 2205/75* (2013.01)

(56) References Cited

U.S. PATENT DOCUMENTS

| | | | |
|---|---|---|---|
| 3,736,927 | A | 6/1973 | Misaqi |
| 3,822,698 | A | 7/1974 | Guy |
| 3,881,198 | A | 5/1975 | Waters |
| 3,998,213 | A | 12/1976 | Price |
| 4,019,508 | A | 4/1977 | Der et al. |
| 4,037,595 | A | 7/1977 | Elam |
| 4,206,644 | A | 6/1980 | Platt |
| 4,233,972 | A | 11/1980 | Hauff et al. |
| 4,297,999 | A | 11/1981 | Kitrell |
| 4,381,267 | A | 4/1983 | Jackson |
| 4,425,501 | A | 1/1984 | Stauffer |
| 4,430,995 | A | 2/1984 | Hilton |
| 4,549,542 | A | 10/1985 | Chien |
| 4,588,425 | A | 5/1986 | Usry et al. |
| 4,590,951 | A | 5/1986 | O'Connor |
| 4,644,947 | A | 2/1987 | Whitwam et al. |
| 4,765,316 | A | 8/1988 | Marshall |
| 4,782,832 | A | 11/1988 | Trimble et al. |
| 4,802,485 | A | 2/1989 | Bowers et al. |
| 4,829,998 | A | 5/1989 | Jackson |
| 4,836,219 | A | 6/1989 | Hobson et al. |
| 4,944,310 | A | 7/1990 | Sullivan |
| 5,035,239 | A | 7/1991 | Edwards |
| 5,046,492 | A | 9/1991 | Stackhouse et al. |
| 5,054,480 | A | 10/1991 | Bare et al. |
| 5,054,484 | A | 10/1991 | Hebeler, Jr. |
| 5,104,430 | A | 4/1992 | Her-Mou |
| 5,113,853 | A | 5/1992 | Dickey |
| 5,154,168 | A | 10/1992 | Schlobohm |
| 5,273,036 | A | 12/1993 | Kronberg et al. |
| 5,284,160 | A | 2/1994 | Dryden |
| 5,303,701 | A | 4/1994 | Heins et al. |
| 5,318,020 | A | 6/1994 | Schegerin |
| 5,349,946 | A | 9/1994 | McComb |
| 5,353,788 | A | 10/1994 | Miles |
| 5,372,130 | A | 12/1994 | Stern et al. |
| 5,377,670 | A | 1/1995 | Smith |
| 5,394,870 | A | 3/1995 | Johansson |
| 5,461,934 | A | 10/1995 | Budd |
| 5,485,851 | A | 1/1996 | Erickson |
| 5,501,212 | A | 3/1996 | Psaros |
| 5,517,986 | A | 5/1996 | Starr et al. |
| 5,533,500 | A | 7/1996 | Her-Mou |
| RE35,339 | E | 10/1996 | Rapoport |
| 5,564,124 | A | 10/1996 | Elsherif et al. |
| 5,564,296 | A | 10/1996 | Theriault et al. |
| 5,577,496 | A | 11/1996 | Blackwood et al. |
| 5,584,296 | A | 12/1996 | Cui et al. |
| 5,649,533 | A | 7/1997 | Oren |
| 5,657,752 | A | 8/1997 | Landis et al. |
| 5,769,071 | A | 6/1998 | Turnbull |
| 5,928,189 | A | 7/1999 | Phillips et al. |
| 5,937,855 | A | 8/1999 | Zdrojkowski et al. |
| 5,950,621 | A | 9/1999 | Klockseth et al. |
| 5,954,050 | A | 9/1999 | Christopher |
| 5,961,447 | A | 10/1999 | Raviv et al. |
| D421,298 | S | 2/2000 | Kenyon et al. |
| 6,050,262 | A | 4/2000 | Jay |
| 6,078,730 | A | 6/2000 | Huddart et al. |
| 6,095,505 | A | 8/2000 | Miller |
| 6,122,773 | A | 9/2000 | Katz |
| 6,135,106 | A | 10/2000 | Dirks et al. |
| 6,179,586 | B1 | 1/2001 | Herb et al. |
| 6,213,119 | B1 | 4/2001 | Brydon et al. |
| 6,349,724 | B1 | 2/2002 | Burton et al. |
| 6,367,474 | B1 | 4/2002 | Berthon-Jones et al. |
| 6,371,112 | B1 | 4/2002 | Bibi |
| 6,393,617 | B1 | 5/2002 | Paris et al. |
| 6,397,845 | B1 | 6/2002 | Burton |
| 6,431,171 | B1 | 8/2002 | Burton |
| 6,435,180 | B1 | 8/2002 | Hewson et al. |
| 6,435,184 | B1 | 8/2002 | Ho |
| 6,470,887 | B1 | 10/2002 | Martinez |
| 6,513,526 | B2 | 2/2003 | Kwok et al. |
| 6,532,960 | B1 | 3/2003 | Yurko |
| 6,561,190 | B1 | 5/2003 | Kwok |
| 6,561,191 | B1 | 5/2003 | Kwok |
| 6,615,831 | B1 | 9/2003 | Tuitt et al. |
| 6,622,311 | B2 | 9/2003 | Diaz et al. |
| 6,622,726 | B1 | 9/2003 | Du |
| 6,626,174 | B1 | 9/2003 | Genger et al. |
| 6,634,864 | B1 | 10/2003 | Young et al. |
| 6,694,978 | B1 | 2/2004 | Bennarsten |
| 6,705,314 | B1 | 3/2004 | O'Dea |
| 6,708,050 | B2 | 3/2004 | Carim |
| 6,709,405 | B2 | 3/2004 | Jonson |
| 6,730,927 | B1 | 5/2004 | Smith et al. |
| 6,733,556 | B1 | 5/2004 | Luigi |
| 6,752,146 | B1 | 6/2004 | Altshuler et al. |
| 6,772,760 | B2 | 8/2004 | Frater et al. |
| 6,772,762 | B2 | 8/2004 | Piesinger |
| 6,793,629 | B2 | 9/2004 | Rapoport et al. |
| 6,854,465 | B2 | 2/2005 | Bordewick et al. |
| 6,881,192 | B1 | 4/2005 | Park |
| 6,889,691 | B2 | 5/2005 | Eklund et al. |
| 6,895,959 | B2 | 5/2005 | Lukas |
| 6,895,962 | B2 | 5/2005 | Kullik et al. |
| 6,918,389 | B2 | 7/2005 | Seakins et al. |
| 6,920,877 | B2 | 7/2005 | Remmers et al. |
| 6,932,084 | B2 | 8/2005 | Estes et al. |
| 6,973,929 | B2 | 12/2005 | Gunaratnam |
| 6,990,980 | B2 | 1/2006 | Richey, II |
| 7,019,652 | B2 | 3/2006 | Richardson |
| 7,069,932 | B2 | 7/2006 | Eaton et al. |
| 7,086,422 | B2 | 8/2006 | Huber et al. |
| 7,089,941 | B2 | 8/2006 | Bordewick et al. |
| 7,096,864 | B1 | 8/2006 | Mayer et al. |
| 7,118,608 | B2 | 10/2006 | Lovell |
| 7,156,090 | B2 | 1/2007 | Nomori |
| 7,178,525 | B2 | 2/2007 | Matula et al. |
| 7,195,014 | B2 | 3/2007 | Hoffman |
| 7,200,873 | B2 | 4/2007 | Klotz et al. |
| 7,204,250 | B1 | 4/2007 | Burton |

(56) References Cited

U.S. PATENT DOCUMENTS 7,255,103 B2 8/2007 Bassin
7,285,090 B2 10/2007 Stivoric et al.
7,297,119 B2 11/2007 Westbrook et al.
7,357,130 B2 4/2008 Broersma
7,357,136 B2 4/2008 Ho et al.
D570,473 S 6/2008 Hamaguchi et al.
7,382,247 B2 6/2008 Welch et al.
7,406,966 B2 8/2008 Wondka
7,406,996 B2 8/2008 Schuh
7,471,290 B2 12/2008 Wang et al.
7,478,635 B2 1/2009 Wixey et al.
7,487,778 B2 2/2009 Freitag
7,516,743 B2 4/2009 Hoffman
7,575,005 B2 8/2009 Mumford et al.
7,588,033 B2 9/2009 Wondka
7,664,546 B2 2/2010 Hartley et al.
7,681,575 B2 3/2010 Wixey et al.
7,738,935 B1 6/2010 Turcott
7,766,841 B2 8/2010 Yamamoto et al.
7,862,521 B1 1/2011 Kodama et al.
7,887,492 B1 2/2011 Rulkov et al.
7,913,692 B2 3/2011 Kwok
7,934,500 B2 5/2011 Madaus et al.
7,942,824 B1 5/2011 Kayyali et al.
7,975,687 B2 7/2011 Gruendler et al.
D643,929 S 8/2011 Dellostritto et al.
8,020,557 B2 9/2011 Bordewick et al.
8,061,354 B2 11/2011 Schneider et al.
8,135,377 B2 3/2012 Baghdasaryan
D659,235 S 5/2012 Bertinetti et al.
8,172,766 B1 5/2012 Kayyali et al.
8,316,848 B2 11/2012 Kwok et al.
8,327,846 B2 12/2012 Bowditch et al.
8,336,546 B2 12/2012 Bowditch et al.
8,353,290 B2 1/2013 Adams
D683,444 S 5/2013 Inoue et al.
D683,445 S 5/2013 Inoue
8,453,640 B2 6/2013 Martin et al.
8,453,681 B2 6/2013 Forrester et al.
8,475,370 B2 7/2013 Mccombie et al.
8,517,017 B2 8/2013 Bowditch et al.
8,591,430 B2 11/2013 Amurthur et al.
D696,393 S 12/2013 Lu
D696,394 S 12/2013 Lu
8,634,891 B2 1/2014 Klomhaus
8,688,187 B2 * 4/2014 DelloStritto ....... A61B 5/14552 600/323
8,720,439 B1 5/2014 Kolkowski et al.
8,733,349 B2 5/2014 Bath et al.
8,740,806 B2 6/2014 Parfenova et al.
8,880,207 B2 11/2014 Abeyratne et al.
8,903,467 B2 12/2014 Sweitzer et al.
8,919,344 B2 12/2014 Bowditch et al.
8,925,546 B2 1/2015 Bowditch et al.
D732,158 S 6/2015 Salmon et al.
D734,446 S 7/2015 Salmon et al.
D740,929 S 10/2015 Pipe et al.
D740,930 S 10/2015 Pipe et al.
9,180,267 B2 11/2015 Bowditch et al.
9,216,264 B2 12/2015 Ho
D776,802 S 1/2017 Loew et al.
9,833,591 B1 12/2017 Ormrod
10,112,025 B2 10/2018 Bowditch et al.
10,632,009 B2 4/2020 Goff et al.
11,660,228 B2 5/2023 Goff et al.
2002/0078958 A1 6/2002 Stenzler
2002/0104541 A1 8/2002 Bibi et al.
2003/0062045 A1 4/2003 Woodring et al.
2003/0079749 A1 5/2003 Strickland et al.
2004/0079373 A1 4/2004 Mukaiyama et al.
2004/0163648 A1 8/2004 Burton
2004/0186681 A1 9/2004 Harle
2004/0226562 A1 11/2004 Bordewick
2005/0005937 A1 1/2005 Farrugia et al.
2005/0028811 A1 2/2005 Nelson et al.
2005/0034724 A1 2/2005 O'Dea
2005/0068639 A1 3/2005 Pierrat et al.
2005/0131288 A1 6/2005 Turner et al.
2005/0133039 A1 6/2005 Wood
2005/0188991 A1 9/2005 Sun et al.
2006/0037613 A1 2/2006 Kwok et al.
2006/0081250 A1 4/2006 Bordewick et al.
2006/0096596 A1 5/2006 Occhialini et al.
2006/0150973 A1 7/2006 Chalvignac
2006/0150978 A1 7/2006 Doshi et al.
2006/0173257 A1 * 8/2006 Nagai ................ A61B 5/14551 600/323
2006/0180149 A1 8/2006 Matarasso
2006/0186149 A1 8/2006 Wu
2006/0231097 A1 10/2006 Dougherty et al.
2006/0249149 A1 11/2006 Meier et al.
2007/0000493 A1 1/2007 Cox
2007/0113854 A1 5/2007 Mcauliffe
2007/0123756 A1 5/2007 Kitajima et al.
2007/0163592 A1 7/2007 Reinstadtler et al.
2007/0169781 A1 7/2007 Tang
2007/0208269 A1 9/2007 Mumford et al.
2007/0221220 A1 9/2007 Bright
2007/0240716 A1 10/2007 Marx
2007/0247009 A1 10/2007 Hoffman et al.
2007/0251527 A1 11/2007 Sleeper
2007/0277825 A1 12/2007 Bordewick et al.
2008/0006275 A1 1/2008 Nickelson et al.
2008/0053451 A1 3/2008 Bordewick et al.
2008/0060649 A1 3/2008 Veliss et al.
2008/0091090 A1 4/2008 Guillory et al.
2008/0127976 A1 6/2008 Acker et al.
2008/0147147 A1 6/2008 Griffiths et al.
2008/0149101 A1 6/2008 Becker et al.
2008/0178879 A1 7/2008 Roberts et al.
2008/0185002 A1 8/2008 Berthon-Jones et al.
2008/0200786 A1 8/2008 Berndsen
2008/0202527 A1 8/2008 Hutchinson et al.
2008/0216831 A1 9/2008 McGinnis et al.
2008/0251079 A1 10/2008 Richey
2008/0304986 A1 12/2008 Kenyon et al.
2009/0044810 A1 2/2009 Kwok et al.
2009/0065005 A1 3/2009 Ades
2009/0078255 A1 3/2009 Bowman et al.
2009/0078258 A1 3/2009 Bowman et al.
2009/0078259 A1 3/2009 Kooij et al.
2009/0194101 A1 8/2009 Kenyon et al.
2009/0241948 A1 10/2009 Clancy et al.
2009/0267242 A1 10/2009 Nichols et al.
2009/0326353 A1 12/2009 Watson et al.
2010/0024811 A1 2/2010 Henry et al.
2010/0083965 A1 4/2010 Virr et al.
2010/0139661 A1 6/2010 Landis
2010/0180895 A1 7/2010 Kwok et al.
2010/0186745 A1 7/2010 Mashak
2010/0191076 A1 7/2010 Lewicke et al.
2010/0206308 A1 8/2010 Klasek et al.
2010/0229867 A1 9/2010 Bertinetti et al.
2010/0240982 A1 9/2010 Westbrook et al.
2010/0312513 A1 12/2010 Mayor et al.
2010/0319687 A1 12/2010 Esaki et al.
2011/0046462 A1 2/2011 Ono et al.
2011/0056489 A1 3/2011 Slaker et al.
2011/0060215 A1 3/2011 Tupin, Jr. et al.
2011/0100366 A1 5/2011 Chou
2011/0105915 A1 5/2011 Bauer et al.
2011/0108031 A1 5/2011 Korneff et al.
2011/0192400 A9 8/2011 Burton et al.
2011/0218409 A1 9/2011 Kugler et al.
2011/0295083 A1 12/2011 Doelling et al.
2012/0016219 A1 1/2012 Fujii
2012/0097156 A1 4/2012 Bowman et al.
2012/0108928 A1 5/2012 Tverskoy
2012/0125334 A1 5/2012 Korneff et al.
2012/0146251 A1 6/2012 Heine et al.
2012/0152239 A1 6/2012 Shikani et al.
2012/0152255 A1 6/2012 Barlow et al.
2012/0167879 A1 7/2012 Bowman et al.
2012/0179005 A1 7/2012 Mccool

(56) References Cited

U.S. PATENT DOCUMENTS

| | | | |
|---|---|---|---|
| 2012/0266873 | A1 | 10/2012 | Lalonde |
| 2012/0298099 | A1 | 11/2012 | Lalonde |
| 2012/0304985 | A1 | 12/2012 | Lalonde |
| 2013/0060098 | A1 | 3/2013 | Thomsen et al. |
| 2013/0104883 | A1 | 5/2013 | Lalonde |
| 2013/0146054 | A1 | 6/2013 | Ho |
| 2013/0239966 | A1 | 9/2013 | Klasek et al. |
| 2013/0263845 | A1 | 10/2013 | Arcilla et al. |
| 2013/0298908 | A1 | 11/2013 | Tang et al. |
| 2013/0333701 | A1 | 12/2013 | Herron |
| 2014/0000600 | A1 | 1/2014 | Dimatteo et al. |
| 2014/0007881 | A1 | 1/2014 | Rummery et al. |
| 2014/0053939 | A1 | 2/2014 | Kaye et al. |
| 2014/0090649 | A1 | 4/2014 | Groll et al. |
| 2014/0102456 | A1 | 4/2014 | Ovizinsky et al. |
| 2014/0127996 | A1 | 5/2014 | Park et al. |
| 2014/0144445 | A1 | 5/2014 | Bowditch et al. |
| 2014/0158128 | A1 | 6/2014 | Heimel |
| 2014/0236083 | A1 | 8/2014 | Sims |
| 2014/0275850 | A1 | 9/2014 | Venkatraman et al. |
| 2014/0275888 | A1 | 9/2014 | Wegerich et al. |
| 2015/0040908 | A1 | 2/2015 | Goff et al. |
| 2015/0083136 | A1 | 3/2015 | Grashow et al. |
| 2015/0094552 | A1 | 4/2015 | Golda et al. |
| 2015/0173672 | A1 | 6/2015 | Goldstein |
| 2015/0197378 | A1 | 7/2015 | Miller et al. |
| 2015/0217074 | A1 | 8/2015 | Wells et al. |
| 2015/0352299 | A1 | 12/2015 | Cortez et al. |
| 2015/0367092 | A1 | 12/2015 | Goff et al. |
| 2016/0015916 | A1 | 1/2016 | Goff et al. |
| 2016/0015918 | A1 | 1/2016 | Kuriger et al. |
| 2016/0120465 | A1 | 5/2016 | Parfenova et al. |
| 2017/0143931 | A1 | 5/2017 | Zheng et al. |
| 2017/0216552 | A1 | 8/2017 | Goff et al. |
| 2018/0021535 | A1 | 1/2018 | Goff et al. |
| 2019/0142625 | A1 | 5/2019 | Goff et al. |
| 2020/0163794 | A1 | 5/2020 | Goff et al. |

FOREIGN PATENT DOCUMENTS

| | | | |
|---|---|---|---|
| CN | 103181835 | A | 7/2013 |
| CN | 103648567 | A | 3/2014 |
| CN | 103690168 | A | 4/2014 |
| CN | 104257368 | A | 1/2015 |
| CN | 104768450 | A | 7/2015 |
| CN | 204520625 | U | 8/2015 |
| CN | 105078426 | A | 11/2015 |
| CN | 105559760 | A | 5/2016 |
| FR | 2853838 | A1 | 10/2004 |
| KR | 10-1601895 | B1 | 3/2016 |
| WO | 91/19527 | A1 | 12/1991 |
| WO | 99/13931 | A1 | 3/1999 |
| WO | 99/21602 | A1 | 5/1999 |
| WO | 99/21802 | A1 | 5/1999 |
| WO | 02/85417 | A2 | 10/2002 |
| WO | 2007/149446 | A2 | 12/2007 |
| WO | 2008/028247 | A1 | 3/2008 |
| WO | 2008/132736 | A2 | 11/2008 |
| WO | 2009/124076 | A1 | 10/2009 |
| WO | 2010/107913 | A2 | 9/2010 |
| WO | 2011/127385 | A1 | 10/2011 |
| WO | 2014/210588 | A1 | 12/2014 |

OTHER PUBLICATIONS

Colrain et al.; The use of a nasal resistance valve to treat sleep disordered breathing (Abstract No. 0518) Sleep 2008 22nd Ann Mtg Assoc Prof Sleep Soc LLC; Balimore MD; vol. 31, Abstract Suppl; p. A172, Jun. 7-12, 2008.

Extended European Search Report received for European Application No. 17800245, mailed on Aug. 11, 2020, 8 pages.

Goff et al.; U.S. Appl. No. 15/329,150 entitled "Portable pap device with humidification," filed Jan. 25, 2017.

Gunaratnam et al.; U.S. Appl. No. 60/494,119 entitled "Nasal Assembly," filed Aug. 12, 2003 (119 pgs.).

Hofsoy et al,; Monitoring and therapy of sleep related breathing disorders; IEEE; 6th Ann. Workshop on Wearable Micro and Nano Technologies for Personalized Heath (pHealth); pp. 41-44; Jun. 24-26, 2009.

International search Report and written opinion received for PCT application No. PCT/US2017/033563, mailed on Sep. 28, 2017, 11 pages.

Invitation to Pay Additional Fees received for PCT application No. PCT/US2017/033563, mailed on Jul. 24, 2017, 2 pages.

Kwok, Philip R.; U.S. Appl. No. 60/505,718 entitled "Ventilator mask and system," filed Sep. 25, 2003 (37 pgs.).

Massie et al,; Acceptance and adherence of a novel device in the treatment of mild to moderate obstructive sleep apnea (Abstract No. 0644); Sleep 2008 22nd Ann, Mtg. Assoc. Prof. Sleep S5c, LLC; Baltimore, MD; vol. 31, Abstract Suppi.; p. A211; Jun. 7-12, 2008.

Oksenberg et al.; Association of body position with severity of apneic events in patients with severe non-positional obstructive sleep apnea; Chest; 118(4); pp. 1018-1024; Oct. 2000.

Penzel et al.; Effect of sleep position and sleep stage on the collapsibility of the upper airways in patients with sleep apnea; Sleep; 24(1); pp. 90-95; Feb. 2001.

Pevernagie et al.; Relations between sleep stage, posture and effective nasal CPAP levels in OSA; Sleep; 15(2); pp. 162-167; Apr. 1992.

Rosenthal et al,; A novel expiratory pressure device to treat mild-moderate OSA (Abstract No. 0634); Sleep 2008 22nd Ann. Mtg. Assoc. Prof. Sleep Soc., LLC; Baltimore, MD; vol. 31, Abstract Suppl.; p. A208; Jun. 7-12, 2008.

Office Action and search report received for Chinese Patent Application No. 201780030535.5, mailed on Aug. 2, 2021, 8 pages (4 pages of English Translation and 4 pages of Original Document).

Office Action and search report received for Chinese Patent Application No. 201780030535.5, mailed on Dec. 1, 2020, 21 pages (11 pages of English Translation and 10 pages of Original Document).

* cited by examiner

POSITIONAL OBSTRUCTIVE SLEEP APNEA DETECTION SYSTEM

CROSS REFERENCES

The present application for patent is a continuation of U.S. patent application Ser. No. 16/775,121 by GOFF et al., entitled "POSITIONAL OBSTRUCTIVE SLEEP APNEA DETECTION SYSTEM," filed Jan. 28, 2020, which is a continuation of U.S. patent application Ser. No. 16/195,624, by GOFF et al., entitled "POSITIONAL OBSTRUCTIVE SLEEP APNEA DETECTION SYSTEM," filed Nov. 19, 2018, which is a continuation of International Application No. PCT/US2017/033563, by GOFF et al., entitled "POSITIONAL OBSTRUCTIVE SLEEP APNEA DETECTION SYSTEM," filed May 19, 2017, which claims the benefit of U.S. Provisional Application No. 62/338,920, by GOFF et al., entitled "POSITIONAL OBSTRUCTIVE SLEEP APNEA DETECTION SYSTEM," filed May 19, 2016, the disclosures of which are incorporated by reference in their entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Obstructive sleep apnea (OSA) occurs when tissue in the upper airway blocks the airway during sleep. The brain will sense the rise in CO2, and will wake up the person so that breathing resumes. Such an event is called an apnea. A partial airway blockage causing an awakening is called a hypopnea. A person is unlikely to remember such awakenings, but sleep is disrupted. The severity of obstructive sleep apnea is measured by the frequency of awakenings, as shown in the table below.

Untreated, OSA not only leaves patients chronically fatigued, but it also carries significant health consequences. Unfortunately, despite a very high prevalence of OSA in the population, the vast majority of sufferers remain undiagnosed. Some estimates put the number of people with obstructive sleep apnea who are undiagnosed as high as 85%. In the US alone, this could mean 35 million undiagnosed sufferers. This large undiagnosed population is one of the biggest public health issues in sleep medicine.

There are many reasons for the low rate of diagnosis. The field of sleep medicine is relatively new. Awareness of clinical sleep problems and their causes remains relatively low. The understanding of sleep-disordered breathing is still advancing at a consistent rate, and will increase awareness further as more clinical consequences are characterized. Further, among some of the population there is a misconception that sleep-disordered breathing is not a serious condition, and is often dismissed as simple snoring. Awareness of the condition is presently significantly lower than the severity warrants.

A further impediment to diagnosis is the relatively onerous process through which most sufferers must pass to get diagnosed. Typically, an initial physician visit is followed by a second visit to a sleep specialist, and then an in-lab polysomnogram (PSG). Polysomnography is a very thorough observation while the user is sleeping. It is conducted in a laboratory setting, with a minimum of 22 electrodes and sensors placed on the patient, and with observation via video throughout the night. Many patients find this foreign sleep environment and observation inconvenient and intrusive. The very nature by which the data is gathered interferes with the typical, natural sleep habits of the test subject. Many labs also have long wait times for studies, especially for weekend studies, which are preferred by some patients to try to reduce the amount of disruption to their work routine. In-lab PSG studies also carry a high cost, often $2000-3,000 per night, a significant burden to the healthcare system. More recently, home sleep testing (HST) devices have been utilized to bring 4-8 channels of the traditional lab test into the home environment. Unfortunately, they still require a prescription, are not simple to use, and result in insufficient data about 20% of the time due to incorrectly placed or inadequately secured electrodes.

Some sufferers report not wanting to go through the whole process of the PSG only to find out the bad news of an apnea diagnosis. This form of wishful denial hinders the rate of diagnosis and postpones the initiation of treatment and its benefits. Many sufferers persist for years, suspecting they might have sleep apnea, but not acting to undertake the testing. This results in significantly increased healthcare spending, and reduced quality of life. Studies have calculated the cost of increased healthcare utilization by undiagnosed sleep apnea sufferers between $2000 and $12,000 additional USD per year. One study estimated the total economic cost of OSA (diagnosed and undiagnosed) to be between $65 and $165 billion annually. There are many impacts of sleep apnea that are difficult to fully estimate, such as the effect on interpersonal relationships of the sufferer.

In addition to these shortcomings, the PSG also has the challenge of trying to understand a complex patient given only one night of data. Due to the inconvenience and expense of PSG, most patients are only studied for one night. However, sleep quality can vary tremendously on a night-to-night basis. Many factors can influence sleep differently each night: exercise, diet, alcohol, stress, environment. It is a significant limitation of the PSG to only gather one night of data. Ideally, data would be gathered from each night of sleep throughout the typical fluctuations by these factors to more completely characterize a patient's sleep.

For those who do get diagnosed, the frontline therapy is Positive Airway Pressure (PAP). It is also called Continuous Positive Airway Pressure (CPAP), or Automatic Positive Airway Pressure (APAP). This disclosure refers to all such therapies as "PAP." PAP is the most widely used and the most effective treatment for OSA. In PAP, a bedside compressor supplies pressurized air to the patient's airway through a hose and mask. The air pressure is set sufficiently high to maintain an open airway during sleep. The clinical data show significant benefit to the use of PAP therapy. Many patients report significant positive impact on their health and quality of life. However, many patients do not feel the benefit of PAP therapy all the time. This can lead to a patient perception that the treatment is not effective, despite significant clinical evidence to the contrary. Some such patients then discontinue therapy, or only use it sporadically. The clinical data show that consistent use of PAP therapy yields the most benefit. Unfortunately, for these sporadic users, there is no convenient way to determine if the therapy is actually working, beyond user perception.

There is another category of patient who will use PAP therapy consistently for a while, then discontinue use once feeling good, assuming that they might be cured, or no longer need PAP treatment. Shortly thereafter they will again feel the fatigue and cognitive impairment reminiscent of their time before PAP therapy. Once they recognize this, they return to therapy. Some healthcare providers have termed this the yo-yo group, as they vacillate on and off therapy like a toy yo-yo going up and down.

Unfortunately for all PAP users, there is no convenient way to ascertain in a scientifically sound manner the effect of using and not using their PAP device on a nightly basis.

Sleeping position plays a very significant and greatly underappreciated role in Obstructive Sleep Apnea. When sleeping in a supine position, gravity's effect on the tongue, tonsils, soft palate and other structures of the upper airway is more pronounced. Clinical studies have shown that the majority of sleepers have at least twice as many blockages when back sleeping compared to side sleeping. The blockages that occur while supine sleeping are more severe: they last longer and result in more significant dips in blood oxygen levels. For some patients, the ratio of supine Apnea-Hypopnea Index ("AHi") to lateral AHi exceeds 4 to 1. Sleeping position is one of the greatest determinants of the likelihood of an apnea or hypopnea occurring. Consequently, sleeping position is also one of the strongest determinants of PAP pressure needed to maintain a patent airway. During an in-lab titration study, PAP pressure settings are determined during REM stage, supine position sleeping. This is because during REM stage, supine sleeping the airway is most prone to collapse. Thus, PAP pressure settings are classically set to cover the worst-case scenario conditions. In fact, a titration study is not considered successful unless REM supine sleep is present. During some studies, technicians will enter the room and push the patient onto their back in order to capture REM supine sleep and the related pressure setting.

Studies have shown that a patient's required PAP pressure is significantly lower when not sleeping supine. One study found that the required pressure during side sleeping for all patients, not just those with positional OSA, was almost 3 cm $H_2O$ lower. For those with positional OSA, the pressure difference between back and side can be much larger.

Studies are not required for most people to recognize the role of sleeping position on breathing. For centuries, it has been reported that people sleep louder when supine, and common advice suggests elbowing a loud snorer to get them off their back to quiet down.

Despite all this evidence, the role of sleeping position in OSA remains a mystery to the vast majority of OSA sufferers. Very few sufferers understand what role sleeping position plays in their apnea.

Accordingly, there is a compelling need for a way to determine the role of position, and the severity of oxygen desaturations in a convenient way. This has application for the undiagnosed as well as the diagnosed, those who are adherent to PAP therapy as well as those who find PAP therapy difficult to consistently use. All would benefit from a better understanding of their OSA, the role of sleeping position, and the nightly impact of their therapy. Beyond PAP therapy, the ability to understand the efficacy of alternative treatments for OSA and the role of sleeping position therein is also of great benefit.

SUMMARY OF THE DISCLOSURE

The present invention provides a positional obstructive sleep apnea detection system that obtains information about a subject's sleep position (e.g., sleeping on the back, sleeping on the side) and combines it with information indicative of a cessation or reduction in breathing (e.g., blood oxygen levels). In some embodiments, the detection system combines a pulse oximeter with a position sensor, optionally together in the same device or housing. Pulse oximetry is at the core of every sleep study to track blood oxygen saturation through the night. Significant apneas will usually drop blood oxygen saturation below standard levels. Some other embodiments may add optional other detectors to detect and possibly analyze, e.g., snoring sounds (microphone and/or accelerometer), respiratory rate (accelerometer and/or heart rate algorithm), respiratory effort (accelerometer, heart rate, and/or microphone), sleep/wake cycles (heart rate and/or accelerometer), airflow at the nasal opening (thermistor, flow sensor and/or pressure sensor). Some or all of this information may be used, e.g., to assess risk of, and possibly diagnose, sleep disordered breathing (especially sleep apnea). It may also be used by the subject to assess CPAP efficacy.

One aspect of the invention provides an obstructive sleep apnea detection device including an optical engagement surface adapted to engage a user's skin; a light source adapted to emit light from the optical engagement surface; a photodetector adapted to detect light at the optical engagement surface and to generate a detected light signal; a position sensor adapted to determine patient sleeping position; a controller adapted to determine and record in memory raw detected light signal values of, or blood oxygen saturation values computed from, the detected light signal and user position information from the position sensor; and a housing supporting the optical engagement surface, the photodetector, the light source, the position sensor, and the controller. In some embodiments, the device also includes an optional a communicator, such as a wireless transmitter or display, adapted to communicate the blood oxygen saturation values and user information position information. In some or all of these embodiments, the optical engagement surface may be shaped to engage skin on a forehead of the user.

In some or all of these embodiments, the housing also has a peripheral surface surrounding the optical engagement surface, the optical engagement surface extending downward from the peripheral surface. For example, the optical engagement surface may be disposed 0.1 mm to 2.5 mm from the peripheral surface, or 0.25 mm to 0.75 mm from the peripheral surface. The device may also have a flexible material disposed below the peripheral surface, with the optical engagement surface extending downward from a lower surface of the flexible material. The flexible material may optionally include an adhesive.

In some embodiments, the optical engagement surface may include a material preferentially absorbing light wavelengths corresponding to light wavelengths emitted by the light source. In some embodiments, the light source is configured to emit light through a light source opening in the optical engagement surface and the photodetector is configured to detect light through a photodetector opening in the optical engagement surface, the light source opening and photodetector opening being disposed 5 mm-10 mm apart. In some embodiments, the device has a tapered frustoconical surface extending from an opening in the optical engagement surface to an active surface of the photodetector, and the diameter of the frustoconical surface adjacent the photodetector may optionally be smaller than a diameter of the active surface of the photodetector. Some embodiments may have an opening in the housing adjacent the light source, the opening having a diameter smaller than a diameter of an active area of the light source.

In some or all of these embodiments, the position sensor includes an accelerometer. In some or all embodiments, the position sensor includes a set of instructions used by the controller to compute patient position from the detected light signal or from the blood oxygen saturation values.

Another aspect of the invention provides an obstructive sleep apnea detection device including: an optical engagement surface adapted to engage a user's skin; a light source adapted to emit light through a light source opening in the optical engagement surface; a photodetector adapted to detect light through a photodetector opening in the optical engagement surface and to generate a detected light signal; a position sensor adapted to determine patient sleeping position; a controller adapted to determine and record in memory blood oxygen saturation values computed from the detected light signal and user position information from the position sensor; and a housing supporting the optical engagement surface, the photodetector, the light source, the position sensor, and the controller, the housing comprising a peripheral surface surrounding the optical engagement surface, the optical engagement surface extending 0.1 mm to 2.5 mm downward from the peripheral surface.

In some embodiments, the optical engagement surface is disposed 0.25 mm to 0.75 mm from the peripheral surface. Some embodiments also include an optional a flexible material disposed below the peripheral surface, the optical engagement surface extending downward from a lower surface of the flexible material. The flexible material may include an adhesive.

In some or all of these embodiments, the light source opening and the photodetector opening are disposed 5 mm-10 mm apart.

Some or all of these embodiments may also include a communicator adapted to communicate the blood oxygen saturation values and user information position information, such as, e.g., a wireless transmitter disposed in the housing. In some embodiments, the optical engagement surface includes a material preferentially absorbing light wavelengths corresponding to light wavelengths emitted by the light source.

Some or all of these embodiments may also include a tapered frustoconical surface extending from the photodetector opening to an active surface of the photodetector. A diameter of the frustoconical surface adjacent the photodetector may be smaller than a diameter of the active surface of the photodetector. In some embodiments, the light source opening has a diameter smaller than a diameter of an active area of the light source.

In some embodiments, the position sensor includes an accelerometer, and in some embodiments, the position sensor includes a set of instructions used by the controller to compute patient position from the detected light signal.

Yet another aspect of the invention provides a method of obtaining obstructive sleep apnea information from a subject. In some embodiments, the method includes the following steps:

placing an optical engagement surface of a detection device against a skin surface of the subject (such as, e.g., the subject's forehead); transmitting light through the optical engagement surface into the skin surface of the subject; detecting light from the skin surface of the subject through the optical engagement surface; determining blood oxygen saturation from the detected light; obtaining subject position information with a position detector within the device; and storing the blood oxygen saturation and position information in memory.

Some embodiments include the step of time correlating blood oxygen saturation with position information. Some or all of these embodiments include the step of computing position information from blood oxygen saturation.

Some or all of these embodiments also include the step of communicating the blood oxygen saturation and position information, such as by, e.g., displaying blood oxygen saturation and position information and/or wirelessly transmitting the blood oxygen saturation and position information using an optional transmitter within the device. The method may also include the step of gathering position information from a second position sensor disposed on the subject's torso.

Still another aspect of the invention provides a method of performing a risk assessment of a subject for sleep disorders. In some embodiments the method includes the steps of obtaining sleep questionnaire information about the subject; obtaining blood oxygen saturation information from the subject during sleep; obtaining head position information from the subject during sleep; comparing the sleep questionnaire information, the blood oxygen saturation information and the head position information to a database of historical data; and determining the subject's risk of sleep apnea from the comparing step.

Yet another aspect of the invention provides a method of performing a risk assessment of a subject for sleep disorders. In some embodiments, the method includes the following steps: obtaining sleep questionnaire information about the subject; obtaining blood oxygen saturation information from the subject during sleep; obtaining head position information from the subject during sleep; comparing the sleep questionnaire information, the blood oxygen saturation information and the head position information to a database of data from a population of other subjects; and determining the subject's risk of sleep apnea from the comparing step.

In some embodiments, the invention provides a system for accurate assessment of the risk of obstructive sleep apnea and the analysis of the role of position in the subject's obstructive sleep apnea. In some embodiments, the invention obtains information about the subject's supine sleeping events and lateral sleeping events separately, as well as mixed AHi. The system may be used by the subject at home and does not require the use of a sleep lab.

In some embodiments, the device is powered by a battery, such as a coin cell, alkaline battery, LiPo battery or Li ion battery. The device may have charging circuitry, such as inductive charging circuitry, and it may be USB compatible using spring pins.

In some embodiments, the device may use an accelerometer, a gyroscope or a magnetoscope to obtain position information.

In some embodiments, the device may send and receive information via a wireless connection using, e.g., a Bluetooth, BLE, Zigbee, 802.11b, RF or other communication protocol, and the information can be sent to and received from a smartphone, which may send information to a network server. The device may also send information over a wired communication link, e.g., when not being worn by a sleeping subject.

In some embodiments, the device has a replaceable disposable adhesive backing that can be removably attached to a reusable electronics housing.

The system described herein allows for multiple nights of data gathering, without interfering with typical sleep habits, and in the comfort of the user's normal sleeping environment. This combination results in sleep data that is more relevant and representative of the user's sleep reality, allowing for more accurate and nuanced identification of sleep issues.

It is well documented that people do not sleep the same each night. Gathering multiple nights of sleep data enables a longitudinal view of sleep. Data gathered using this system can show changes in sleep due to environmental and health factors such as sleep hygiene, weight change, stress, alcohol intake, illness, allergies and exercise. Understanding the factors that influence the variability of sleep quality is critical to accurately addressing sleep disorders.

Further, the systems described herein allow for the collection of data without interfering with normal sleep patterns of the user.

Finally, the user's typical sleep environment is the only relevant test location. When sleeping in a new location, people have different reactions which inevitably influence their sleep quality.

Obstructive Sleep Apnea is position dependent in almost all cases. A person on his or her back will experience more frequent and more severe airway blockages as gravity pulls the tongue, tonsils, soft palate and other structures into the airway. Most OSA patients will experience at least twice as many events when sleeping on their backs as compared to their sides. Some will experience four to five times as many blockages when sleeping supine. In contrast, patients with central sleep apnea and other conditions that cause blood oxygen to drop during sleep are typically less position dependent. Since almost everyone spends time sleeping on both their back and their side, the combination of pulse oximetry data and position data can be used to help differentiate OSA from Central Sleep Apnea (CSA) and other non-position dependent conditions and situations.

The current invention combines sensors for optical measurement with sensors that can determine position. The device can be worn on the skin through the night. The position measuring component may or may not have to be calibrated on a given patient to be able to distinguish back sleeping form side sleeping. This device would record blood oxygen saturation and position for the duration of one or more nights. Then, importantly, this information can be analyzed to compare the frequency and/or severity of apnea events when the patient is back sleeping to the events occurring when the patient is side sleeping. This analysis can occur on the device itself, or on other devices using the data gathered by the device. The analysis can compare the frequency of low blood oxygen saturation events, the severity of those events, or a combination of frequency, severity and/or duration in the two sleeping positions. If the frequency, severity or duration of blood oxygen deficits is significantly greater during back sleeping than side sleeping, the data analysis would indicate OSA, while rough equality in the number, length and severity of blood oxygen deficits could indicate the possibility of CSA or another less common sleep disorder.

In some embodiments, a data graph is generated of blood oxygen saturation over time. The area above the curve, denoting the difference between the patient's recorded blood oxygen saturation and complete (100%) saturation over time, can be used to differentially diagnose OSA and CSA. In patients with OSA, the area above the curve will typically have a higher ratio of events per minute of back sleeping as compared to side sleeping. A patient with CSA and other conditions or situations will have a lower ratio of events per minute supine to lateral. This area above the curve can incorporate the frequency, duration and severity of blood oxygen desaturations.

The system described herein is able to distinguish between Central and Obstructive apnea. In one embodiment, the combination of position data and SpO2 data can be used to determine the degree of Positional Obstructive Sleep Apnea (pOSA). Typically, pOSA is defined as having at least twice the number of events (apnea or hypopnea) when in the supine position. Further, desaturation events occurring in the supine position last longer and reach lower desaturation levels. The invention described herein offers the ability to determine the correlation between the subject's position and each desaturation event. This correlation is important for distinguishing CSA from OSA. OSA is position-driven the majority of the time. Studies have shown that up to 75% of OSA patients are pOSA. Nearly every patient has more events in the supine position. CSA, by contrast, is not nearly so position-driven. Although there are some case reports that CSA can be exacerbated by the supine sleeping position, the vast majority of CSA events are independent of position. Using this knowledge, we can estimate the likelihood that a user has CSA. If a user has significant events, but they are not correlated to the supine sleeping position, then CSA is strongly suspected. For these users, the application can suggest further studies using the device, as well as further studies using other standard of care testing equipment. In one embodiment, if CSA is suspected due to the initial results from the testing, then the user is directed to place the device on their chest for subsequent testing. This testing can be done using the same device and application, saving significant time, money, and convenience. On the subsequent test nights, the user places the device on the chest to gather motion data from that location. For patients with CSA, there is a cessation of breathing effort that is distinct and unique to CSA from OSA. A patient with CSA will have this cessation of breathing, which will show up in the motion data as a significant lapse in breathing effort motion. In this way, the system described herein can very reasonably distinguish OSA and CSA.

EMBODIMENTS

In one embodiment, the sensor can be located on the head or the torso, or both. With a sensor placed on both the head and the torso, more data can be gathered, and more subtle observations can be drawn from the comparison of the data from the two locations. The head sensor, for example on the forehead, can gather head position, pulse oximetry, and sound data. The sensor on the torso can be placed anywhere on the neck, clavicle, chest, belly, diaphragm. The torso sensor can detect motion and position data. From this data, the body position, respiratory rate, respiratory effort and heart rate can be determined.

One advantage of a second sensor on the chest area is that it can provide data on respiratory effort. Often during an apnea, there is increased respiratory effort as the body tries to get more oxygen but cannot due to the blockage. This effort is pronounced and can be captured by a motion sensor on the torso. Adding this additional channel capability can also satisfy testing channel requirements for certain health systems.

In another embodiment, the same sensor device is worn over multiple nights. Multiple nights of data helps accumulate additional information about the user's sleep quality. As sleep quality varies nightly, multiple nights of data provide a much stronger indication of the user's sleep issues.

In one embodiment, the sensor is worn on the head for multiple nights to gather baseline information on the user's sleep, such as oxygenation, movement, and respiratory disturbances. Once this pattern has been established, the same sensor can then be worn on the torso, chest, or belly. In this location, the sensor will detect the movement of the diaphragm and chest corresponding to respiratory effort. If the sensor detects long pauses of movement, this is an indication of possible central sleep apnea. In this way, the same device can be used over multiple nights in two different locations to differentiate between OSA and CSA.

The system consists of wearable sensors, a data analysis platform and algorithms, and a user interface for gathering user input and communicating results.

Wearable Sensors

The device includes optical sensors for obtaining a photoplethysmography (PPG) signal. Light is emitting into the tissue in at least two different wavelengths. The resulting light reflected back into the optical sensor is measured at each wavelength. The results are compared to determine the oxyhemoglobin concentration. The optical sensors enable measuring blood oximetry, pulse rate and heart rate variability (HRV).

The device also includes sensors for determining position and acceleration. In a preferred embodiment, this is done by an accelerometer. The accelerometer data is used to determine head position of the sleeper. As discussed herein, sleeping position is of critical importance for respiratory sleep disorders. Motion data can also be used to identify restless leg syndrome (RLS), a sleeping disorder that involves urges to move the legs. Accelerometer data can also indicate wake and sleep intervals of the user, and be used to calculate total sleep time. RLS is characterized by the urge and sensation to move the legs during sleep and sleep transitions. The unique signature of RLS movement is detectable in the accelerometer data. RLS movements are jerky and repetitive, which can be discerned from a typical sleeping motion signal. In one embodiment, RLS risk can be assessed from user-inputted data on a companion app or questionnaire, or from measurements and signatures in the forehead accelerometer data. Then, if RLS is suspected, additional night(s) of observation and measurement with the device can be done, with the device placed on the legs to measure movement. This approach can confirm suspected RLS with great certainty, due to the exceptionally pronounced motion signal on the legs during RLS events. Actigraphy is the study of motion data to determine physiologic events. In one embodiment, motion data from the accelerometer is used to determine sleep stage. During REM sleep, the user is typically nearly motionless, due to the body's protective mechanism to prohibit acting out one's dreams. Thus, motion data can discern suspected REM stage sleep from times of little or no motion. During Stage 1 and 2 sleep, the respiratory signal, found in the motion data, slows as the users transitions to sleep.

The user's sleeping position can also be determined from the PPG waveform gathered by the device. The waveform characteristic changes depending on sleeping position from supine sleep to lateral sleep. Even the right and left lateral sleeping positions are distinguishable. As typical sleepers change position 20 or more times each night, the device will typically have many opportunities to assess what each position looks like on the PPG waveform.

Since the sleeping position affects the PPG waveform, it is also advantageous to use the position data gleaned from the accelerometer to inform the processing of the PPG data. For instance, since we know the amplitude of the AC component of the PPG is reduced in the side-lying position, we can use different filters to process the PPG in this circumstance to yield more accurate Sp02 results. Correspondingly, when the accelerometer data indicates that the user is supine sleeping, we can process the PPG signal accordingly with the knowledge that the amplitude will be larger.

The device can determine when a user sits up, stands up, and leaves the bed. This is especially useful for tracking visits to the bathroom in the night. Nocturia, the nighttime urge to urinate, is a symptom of sleep apnea. Once using treatment such as CPAP, many users report a reduction in nocturia. The device is able to quantify this reduction, offering positive reinforcement to the user.

The motion data gathered by the accelerometer can also be used to strengthen the measurements from the oximeter. In pulse oximetry, significant error in the signal can be created during motion events. Using the motion sensor, these motion events can be identified. In one embodiment, the device algorithm will flag Sp02 values that are calculated from data gathered during a motion event as determined by the motion sensor. In one embodiment, the algorithm will discard Sp02 values that are associated with motion events above a threshold that renders the Sp02 significantly less accurate. Under typical use, the sensor will be able to achieve accuracy within about +/−3% for Sp02. Data gathered during motion events that reduce the accuracy beyond a threshold, such as +1-5%, may be discarded. In another embodiment, when there is a motion a different set of coefficients is used to calculate the Sp02 which take into account motion circumstances.

In one embodiment, the PPG signal itself is used to determine when there are motion events and to consequently filter out the calculations for the Sp02. Motion events show up in a pronounced way in the PPG waveform as an increased signal to noise ratio. In another embodiment, this motion signature in the PPG can be coupled with the data from the motion sensor to determine when to discard or adjust the Sp02 data calculation.

Motion data can also identify coughing, enabling the measurement of sickness and allergies. Coughing typically results in significant, sudden movement in predominantly one of the 3-axes of accelerometer data. This signature is recognized by the software and recorded as a coughing event. Measuring and tracking coughing empowers users to understand the triggers in their sleeping environment that can lead to disrupted sleep.

In another embodiment, motion data is used to identify vibration caused by snoring. The motion signal signature from snoring is characterized by a steadily increasing vibration lasting a typical 1-2 seconds, and timed to coincide with the respiratory cycle. Snoring will occur up to 15 times per minute, but more typically 6-12 times per minute. The motion data exhibits values that fluctuate as they increase, followed by a more rapid drop off in motion. In some snorers, the data reveal long periods without significant motion, punctuated by much more significant motion events as the pauses are broken with sudden snoring.

The user's respiratory rate can be determined from the device sensor data. The PPG waveform contains adequate signal for the derivation of the respiratory rate using signal processing techniques described in the art. Actigraphy data from the accelerometer is capable of revealing the respiratory rate as well. Respiratory rate shows up as a sinusoidal pattern in the motion data. Respiration rate can be determined from the processing of this signal. Combining the motion data derived from the motion sensor with the PPG signal data can strengthen the accuracy of the respiratory rate calculation. Additionally, respiratory effort, especially when there is respiratory distress, can be determined from the processing of the data. Significantly increased motion in the respiratory signal indicates respiratory distress. This can occur during an apnea or hypopnea, and provides another signal to identify and confirm respiratory events.

In some embodiments, a microphone captures the sound signal, and allows for analysis of snoring sounds and pauses in breath. The microphone can be incorporated in the device. Alternatively, the system can use an existing microphone in a smartphone, phone, tablet, or other connected device.

In some embodiments, the device includes conductive sensors for the forehead for gathering an electroencephalogram (EEG) signal. EEG can be used to indicate brain activity, sleep staging, and identify arousals during sleep.

In some embodiments, pressure and flow sensors are included to assess airflow. This can be realized through the placement of an open tube just beneath the nares, which is in communication with a pressure sensor placed in the device. Alternatively, an additional patch with wireless connectivity can be placed just beneath the nares and utilize pressure, temperature, sound, or flow sensors to assess respiratory airflow. Alternatively, an additional patch placed under the nares can be connected to the device with a thin wire cable for power and/or data communication.

Additional sensors in some embodiments include an ambient light sensor to assess the amount of ambient light in the sleeping environment, gas sensors to assess the amount of key respiratory gases such as $CO_2$ which plays a key role in regulating respiratory drive, and other environmental sensors to assess air quality of the sleeping environment.

The sensor device consists of an electronics housing, electronics, and a flexible skin attachment element. In a preferred embodiment, the electronics housing is reusable and can be recharged. In another embodiment the electronics and housing are disposable. A new flexible skin attachment element can be attached for each use. The flexible skin attachment element can be an adhesive layer beneath the housing. Alternatively it can be a thicker layer with adhesive on both sides and a flexible layer in between made of a spacer material such as foam. In another embodiment the flexible skin attachment element can be an overpatch with an adhesive underside and a means to be applied or all or a portion of the housing to secure it to the user. A further alternative embodiment has the electronics housing located within a headband secured to the forehead. Another embodiment integrates the electronics into an eyeshade. A further embodiment secures the electronics in an ear plug which is fitted partway into the ear canal. Another embodiment incorporates the electronics into a sleep hat, placing the sensor over the forehead.

Sensor Locations

In one embodiment, the device is placed on the forehead. The forehead provides an ideal placement for gathering the signals of interest. In this embodiment, the device may be placed on the upper half of the forehead, closer to the hairline than the eyebrows. The upper forehead has excellent perfusion, resulting in a good signal. The device is placed anywhere aligned between the two eyes, above the eyebrows, and below the hairline. Placement in the upper portion of this described box often results in the best signals. The vasculature of the upper half of the forehead is characterized by multiple smaller vessels resulting in better perfusion. This area has a better AC/DC signal ratio on the PPG, which allows for a better signal to noise ratio.

Other locations where the device can be placed and achieve adequate signal include the ear lobe, the ear canal, behind the ear on the skull, the nostril, the nasal septum, the clavicle, the neck, the laryngeal prominence, the back, the sternum, the chest, or the belly among others.

User Interface

In one embodiment, a smartphone, tablet or similar communication device (hereafter smart device) is integral to the system. An application on the smart device collects information from the user. The application leads the user through a streamlined collection of user data including age, gender, height, weight and self-reported sleep quality. This collection may include a survey based on clinically validated sleep questionnaires such as STOP-BANG, Epworth Sleepiness Scale, Berlin questionnaire. These questions have been shown to identify apnea with good accuracy. Incorporating this data into our system enhances the accuracy of the assessment. Additionally, the application includes certain questions designed to identify individuals who may have more complex sleep disorders and may benefit from a polysomnography test. Questions about leg movements during sleep, as reported by the user or bed partners, can help identify Restless Leg Syndrome (RLS). The application survey may also include questions to identify users with more complicated health issues such as congestive heart failure or pulmonary insufficiency, which necessitate consultation with a physician.

Data Analysis

The data analysis platform takes data from the sensors over one or, preferably, multiple nights and combines it with the results from the questionnaires to create a very accurate, real-world, and personalized assessment of the user's sleep. The ability to combine measured, objective sleep data with user-reported data from validated questions is unique to this device. In one embodiment, the data from the objective measurements will be given priority over the user-reported data. However, in cases where the clinical conclusion from the measured data is not very clear, the subjective user-reported data is used to determine the next step for the user. For example, if the measured overnight Sp02 data does not show significant desaturations, but the user reported data shows significant fatigue and sleep complaint, the application would suggest further study to examine the cause of the fatigue since OSA would not be suspected. In this scenario, the application would suggest investigating further testing for Respiratory Effort Related Arousals (RERA), insomnia, or other sleep disorders. This is just one example to illustrate the power of combining the measured sleep data with user reported data to help determine the cause of sleep issues. This data can optionally be compared to historical controls to give the user an idea of where they stand compared to their peers of similar age, gender, body mass index and sleep habits. Research shows that providing reference to a peer group enhances the impact of the sleep study results and can serve as a powerful motivator for behavior change.

Influencing Behavior

An important function of the system we describe herein is the ability to positively influence user behavior. One key way to achieve this is through a feedback loop about therapy. In addition to identifying and diagnosing sleep apnea, the system can provide feedback on the use of various treatment therapies. A PAP user can use the device to verify the efficacy of the PAP device. If desired, different levels of PAP therapy can be tested and assessed using the device. For newly diagnosed patients, feedback is especially important. The sensor can provide useful feedback for these users. Most new users of PAP therapy fall into one of two categories: those who immediately feel benefit from therapy and quickly become consistent users, and those who feel less acute immediate benefit. For the latter group, quantitative feedback on exactly how much PAP therapy is improving their breathing at night is extremely useful in helping convince them how the benefits outweigh the inconveniences of therapy. With the sensor, they can track their progress on PAP. Research has shown that usage during the first few weeks of PAP therapy is very indicative of long-term adherence.

Users who choose alternative therapies can benefit from the apnea detection system as well. There are several alternatives to PAP therapy. PAP therapy has repeatedly been shown to be the most effective, but only if used. For patients who cannot or choose not to use PAP, some options exist including: oral appliances, surgeries, positional therapy, lifestyle changes, oral pressure therapy. However, the efficacy of these therapies is difficult to assess. Many users are not followed closely or given sleep testing assessment once on these therapies, or following surgery. Consequently, they may be risking their health if their apnea is insufficiently treated. The apnea detection system can be used in conjunction with all alternative therapies to assess their efficacy. This improved access to thorough assessment empowers users to utilize alternative therapies with confidence, or discontinue spending time and money on approaches that do not benefit them.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4A is a perspective view; FIG. 4B is a top view; FIG. 4C is a side view; and FIG. 4D is another side view.

FIG. 5A is an exploded perspective view;

FIG. 5B is a top view; FIG. 5C is an exploded side view; and FIG. 5D is another exploded side view.

DETAILED DESCRIPTION

Figure 1:
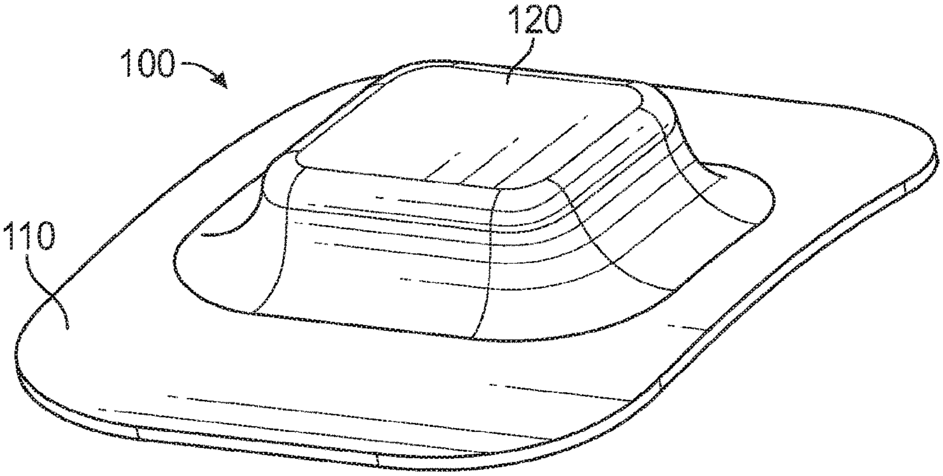
FIG. 1 is a perspective view of a wearable sensor according to an embodiment of the invention.

Referring to FIG. 1, a perspective view of one embodiment of a wearable sensor assembly 100 portion of the system is shown. The housing for the electronics 120 and the flexible skin attachment element 110 are shown assembled together. The electronics housing 120 can be made of a hard plastic, or a softer elastomer, or a combination thereof. The flexible skin attachment element 110 can be made of a foam, fabric, polymer, elastomer, or similar flexible material that is compatible with a skin-contacting application.

Figure 2:
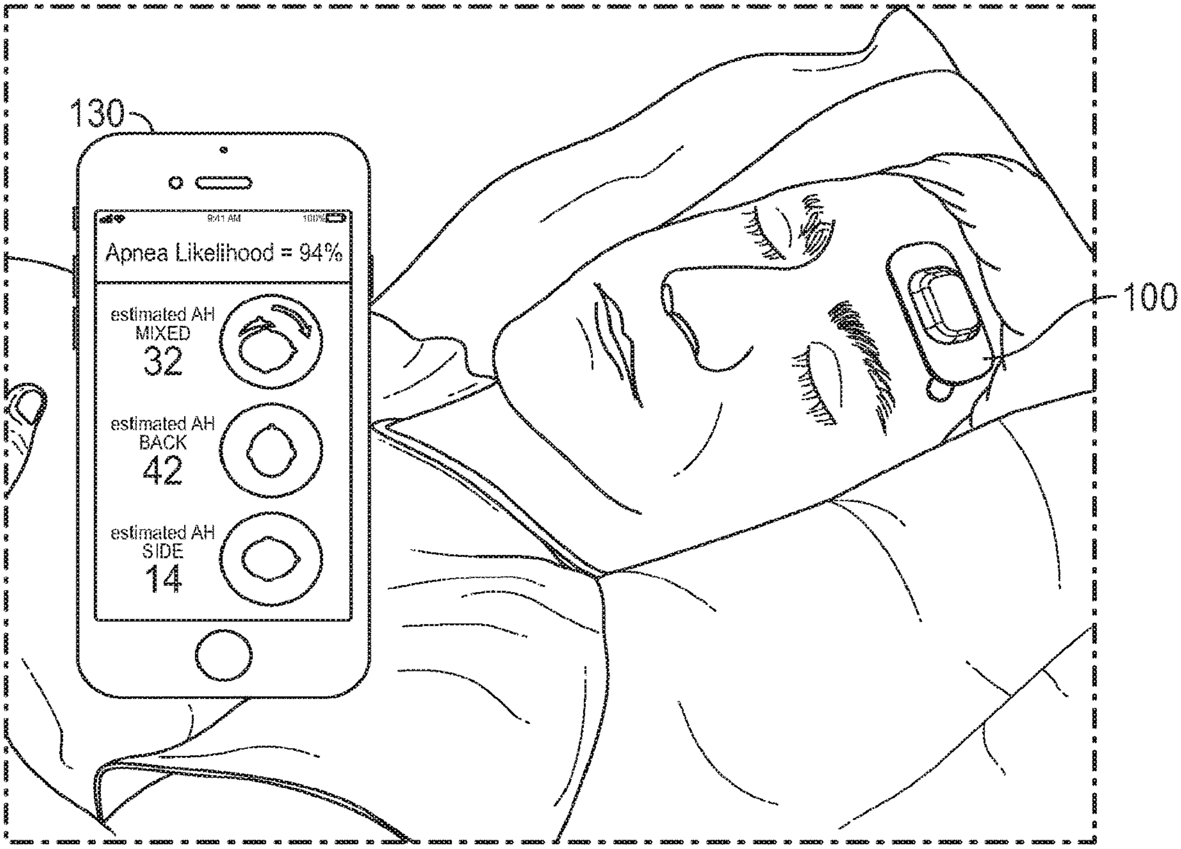
FIG. 2 shows the system in use. The wearable sensor is on the forehead of a user. A smartphone is shown in the foreground, presenting the findings of the sensor.

FIG. 2 shows an embodiment of the system in use. The wearable sensor assembly 100 is shown attached to the forehead of a sleeping user. A smartphone 130 is shown in the foreground displaying the results of the positional sleep apnea assessment by the system. A key feature of the system is shown in FIG. 2: the ability to indicate the degree to which sleep apnea is affected by sleeping position. This information empowers users to better understand and treat their apnea. For example, as shown in FIG. 2, the display of the smartphone 130 provides information about AHi when the user is on his back and on his side as well as the likelihood that the user will experience an apnea event.

Figure 3A:
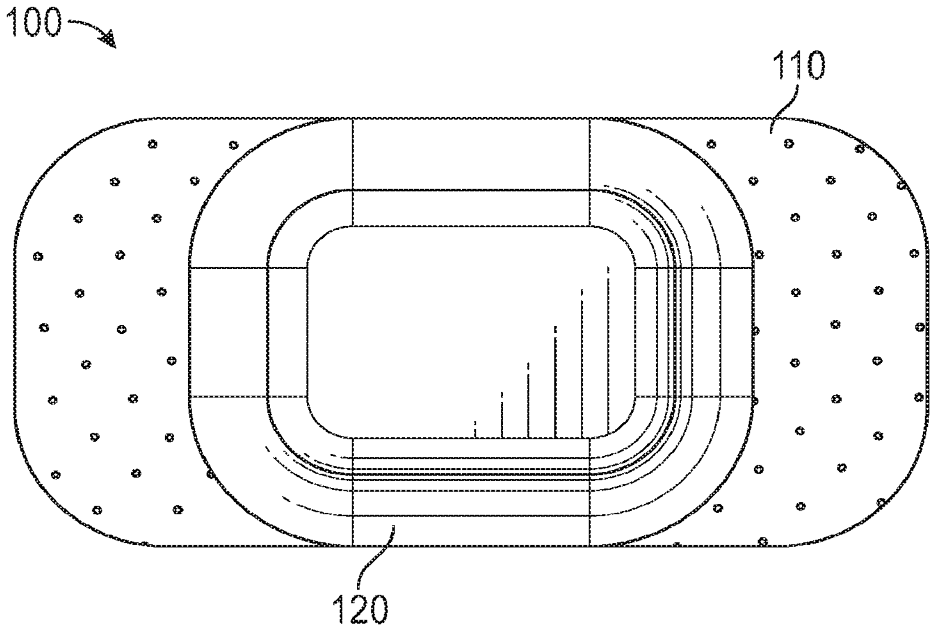
FIGS. 3A and 3B are top views of wearable sensors showing embodiments of the invention.
Figure 3B:
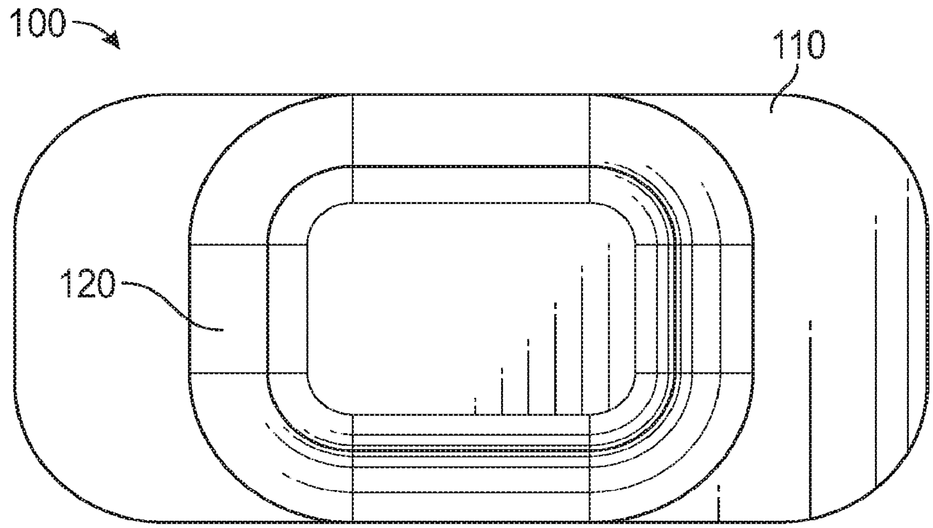

In FIG. 3A an embodiment of the wearable sensor assembly 100 is shown with a flexible skin attachment element 110 made of elastomer or foam. FIG. 3B shows an embodiment of the wearable sensor assembly 100 with a flexible skin attachment element 110 made of fabric, paper, or woven material. In each case, the flexible skin attachment element is constructed to be able to conform to the anatomy of the wearer, particularly to the curvature of the forehead.

Figure 4B:
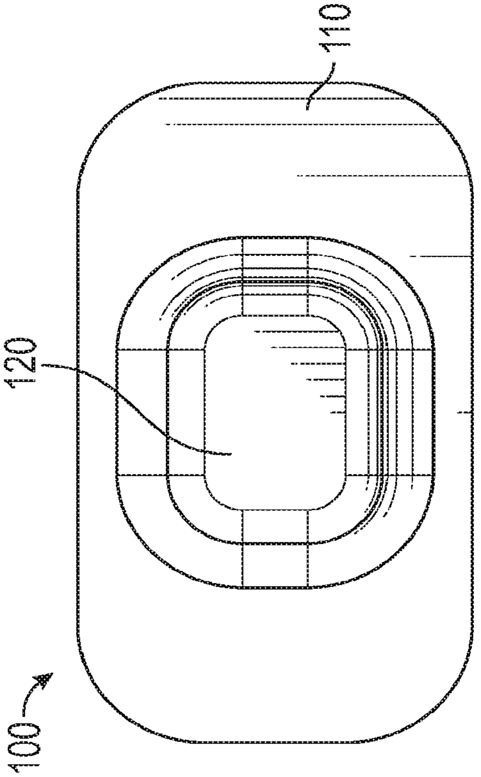
FIGS. 4A, 4B, 4C, and 4D show one embodiment of the wearable sensor in multiple views.
Figure 4D:
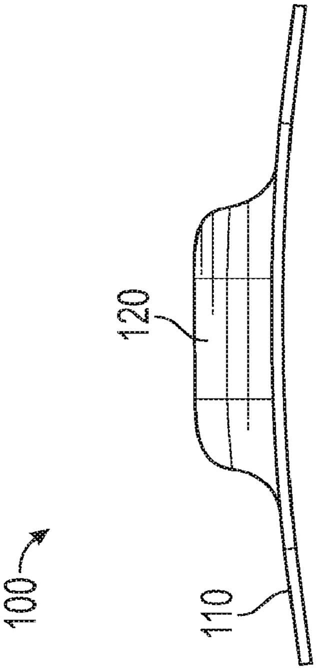
Figure 4A:
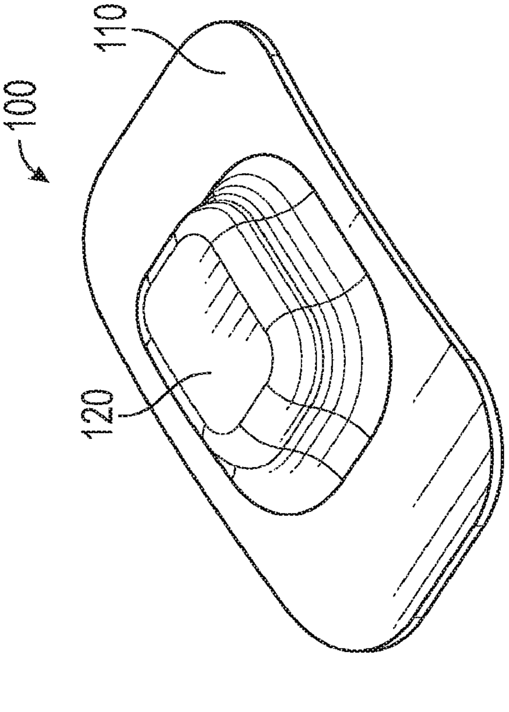

FIG. 4A shows a perspective view of the wearable sensor assembly 100 with the flexible skin attachment 110 and the electronics enclosure 120.

FIG. 4B shows a top view of the wearable sensor assembly 100.

Figure 4C:
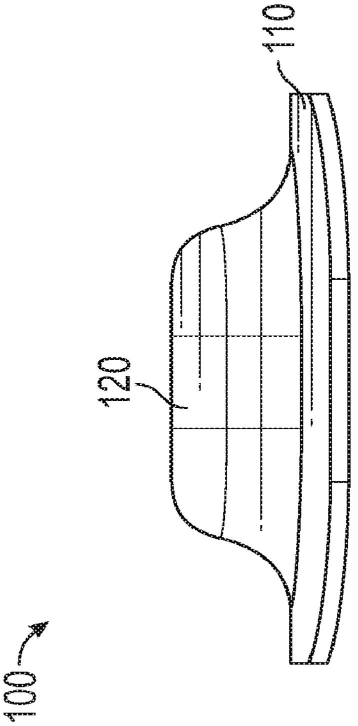

FIG. 4C shows an end view of the wearable sensor assembly 100 illustrating a possible curvature of the flexible skin attachment 110.

FIG. 4D shows a side view of the wearable sensor assembly 100 illustrating a possible curvature of the flexible skin attachment 110.

Figure 5B:
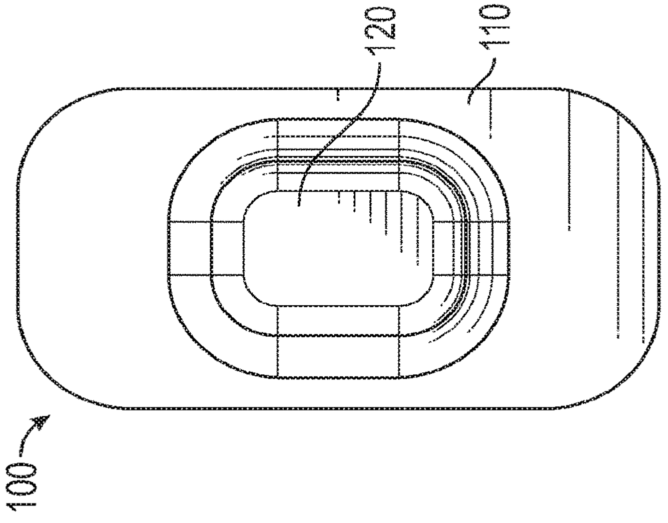
FIGS. 5A, 5B, 5C, and 5D show an embodiment of the wearable two-part sensor having a housing and a skin-contacting element.
Figure 5D:
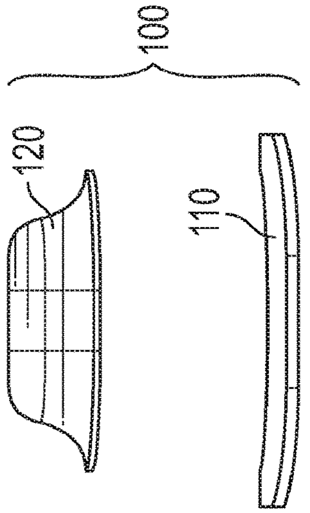
Figure 5A:
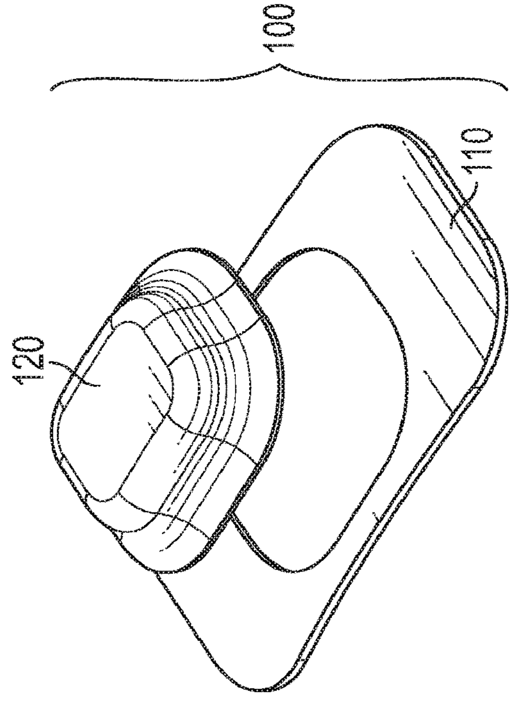

FIG. 5A shows a perspective view of the wearable sensor assembly 100, with the two main elements separated for illustration. The flexible skin attachment element 110 can be placed over the electronics enclosure 120 to secure it to the user.

FIG. 5B shows a top view of the wearable sensor assembly 100.

Figure 5C:
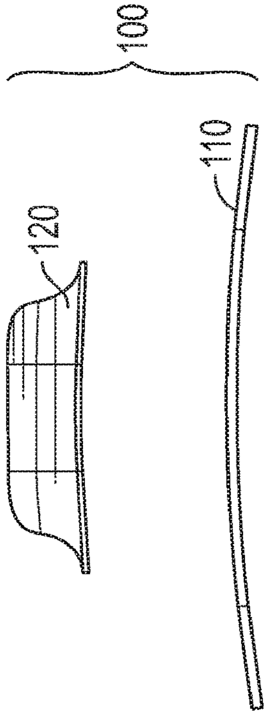

FIG. 5C shows an end view of the wearable sensor assembly 100.

FIG. 5D shows a side view of the wearable sensor assembly 100.

Figure 6:
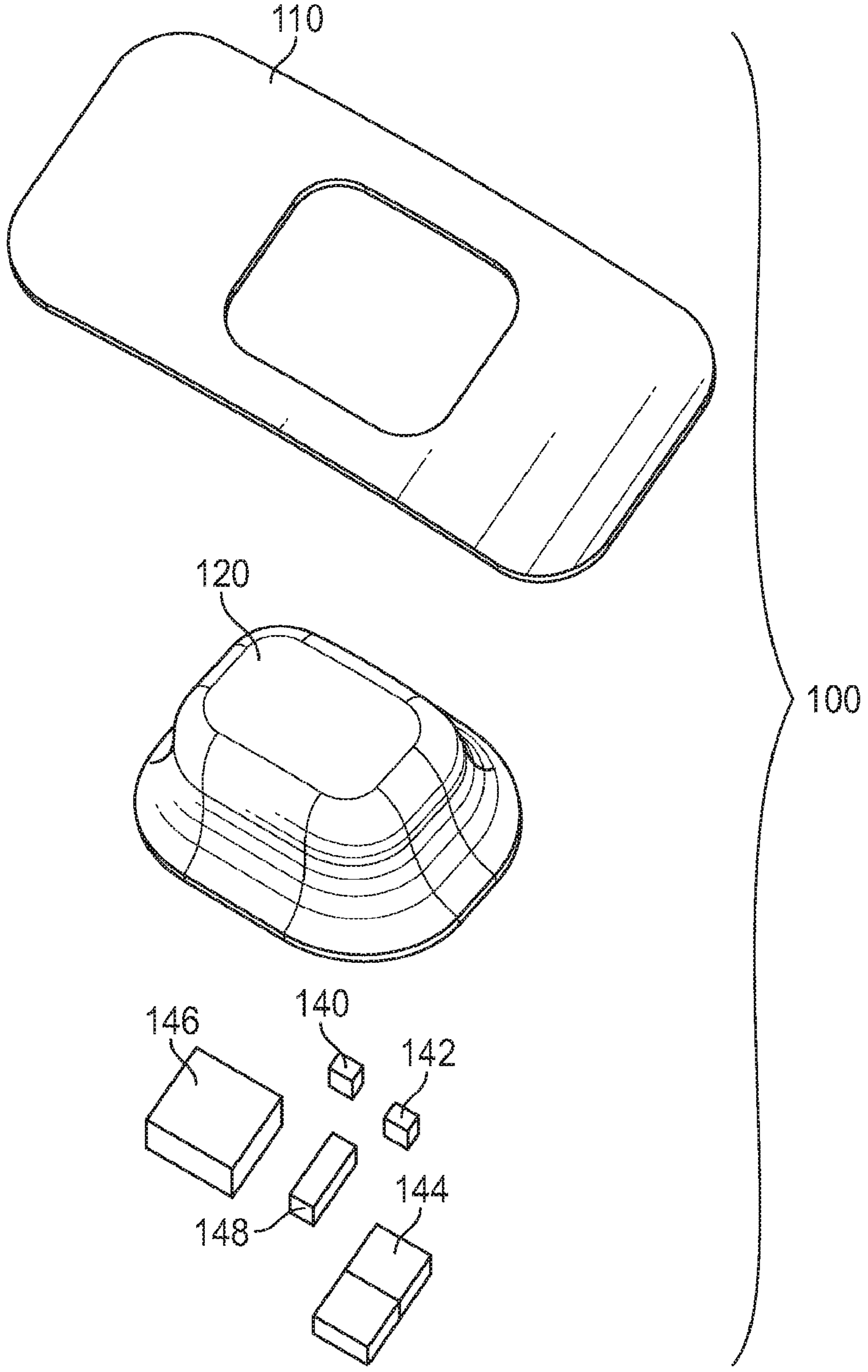
FIG. 6 shows an exploded view of the wearable sensor with the housing, skin-contacting element, and some key internal components.

FIG. 6 shows an exploded view of one possible construction of the wearable sensor assembly 100, illustrating several of the key components. The power supply 146 can be a lithium polymer or lithium ion battery. The power supply 146 could also be a primary cell, coin cell, fuel cell battery, or other rechargeable or single use chemistry cell or cells. The position sensor 140 can be an accelerometer, a 6-axis accelerometer, a magnetometer, gravitometer, gyroscopic sensor or other similar device for determining position, including a mechanical element such as a mercury switch. The wireless connection transmitter and receiver 142 can be a Bluetooth radio, Bluetooth Low Energy (BLE), radio, Zigbee, 802.11b, nRF, GSM, a module containing any of these elements, or other similar component to enable 2-way communication between the wearable sensor and a network or device such as a smartphone. The pulse oximetry measurement can be provided by a pulse oximeter module or individual components selected to perform pulse oximetry per the desired requirements. The pulse oximetry components are shown by 144. Signals from the sensor are sent to a microprocessor 148 for processing. The microprocessor 148 may be selected from a group of microprocessors standardly available of suitable specifications, or it may be custom fabricated specifically for the purpose herein. Memory (not shown) can be integrated as part of the microprocessor 148 or added as a separate component.

Figure 7:
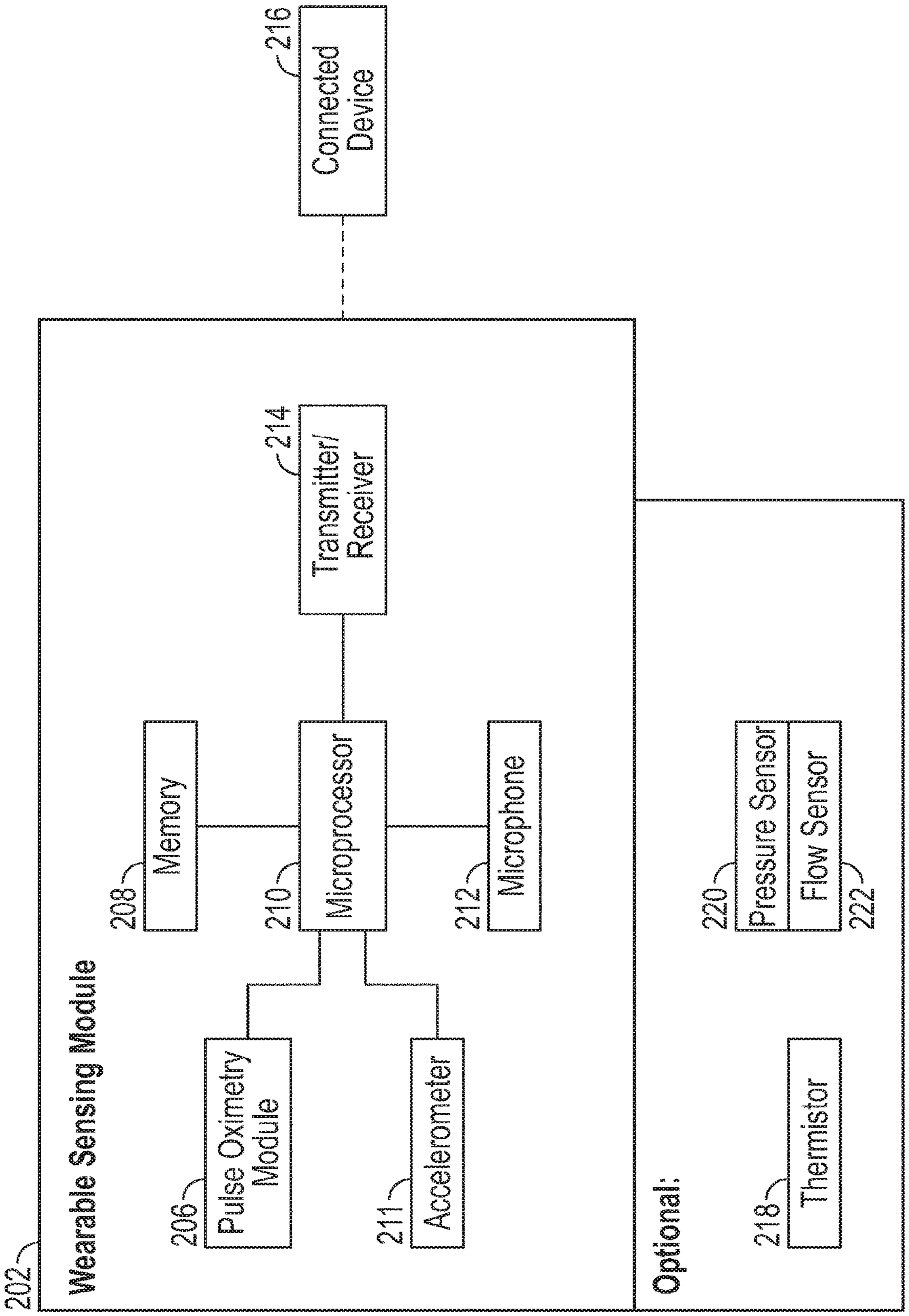
FIG. 7 shows a block diagram of an embodiment of the system.

FIG. 7 is a block diagram showing the key components of the wearable sensing module 202 and their relationships to each other and to a remote connected device 216. Light signals are emitted by the pulse oximetry module 206, and received back by the module 206. These signals are sent to the microprocessor 210 where they are further processed. Additional sensing signals from the accelerometer 211 and microphone 212 are sent to the microprocessor 210 as well. Optionally, a pressure sensor 220 and flow sensor 222 can be added to the system. Flow can be derived by a pressure differential calculation as is known in the art, or by use of a thermistor 218. Pressure measurements and thermistor measurements would be taken just at/near the nostrils. Commonly, such sensors are placed on the upper lip just below the nose. Information from the various sensors and any calculations performed by the microprocessor may be sent wirelessly to a remote connected device 216 (such as, e.g., a smartphone or computer) by a transmitter/receiver 214. Further processing of the data from the sensors and information from the microprocessor may be performed by the connected device 216.

Figure 8:
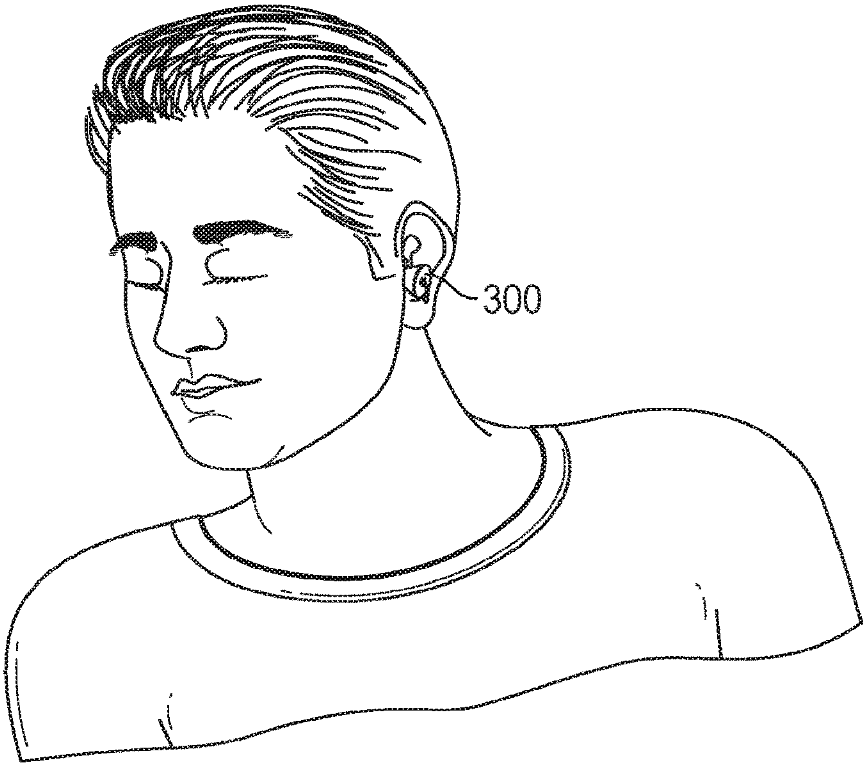
FIG. 8 shows wearable sensor assembly adapted to be placed on the ear lobe.

FIG. 8 shows wearable sensor assembly 300 adapted to be placed on the ear lobe. In this case, the pulse oximetry assembly would use transmittance oximetry instead of reflectance oximetry as is used on the forehead. This arrangement would also allow for the capture of head position during use. The user interface can specify which ear is to be used, or this can be discerned from the accelerometer data and an algorithm.

Figure 9:
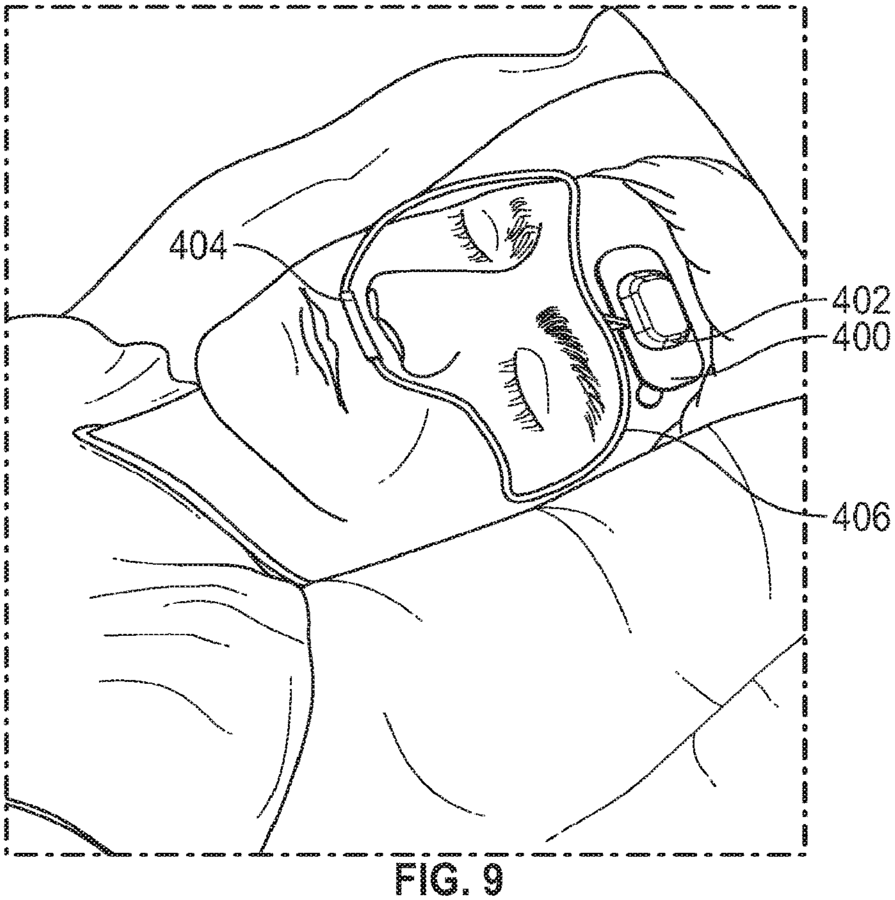
FIG. 9 shows a wearable sensor assembly augmented by a thermistor and/or pressure sensors placed at or near the nostrils.

FIG. 9 shows a wearable sensor assembly 400 augmented by a thermistor and/or pressure sensors in a housing 404 placed at or near the nostrils. The sensors in housing 404 communicate with the forehead mounted sensor housing 402 via conductors 406. The device is shown with the nostril sensors and the forehead wearable sensor assembly. Alternatively, and not shown, the pressure and flow data could be coupled to an ear-worn sensor assembly.

Further, the thermistor and pressure and flow sensors could be housed in a separate assembly with its own power supply, memory, processor, and wireless communication capability.

Figure 10C:
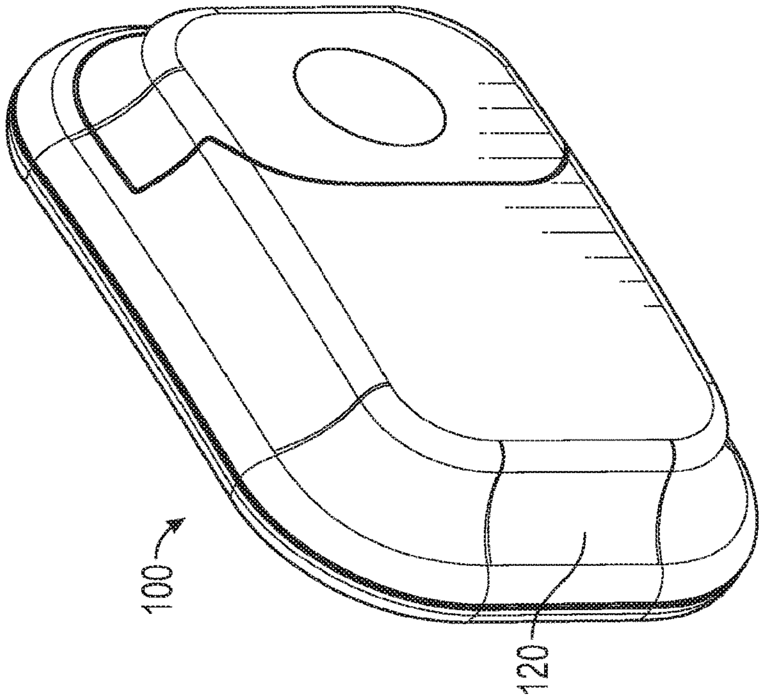
FIG. 10C shows a perspective view of the wearable sensor assembly of FIG. 10A.
Figure 10A:
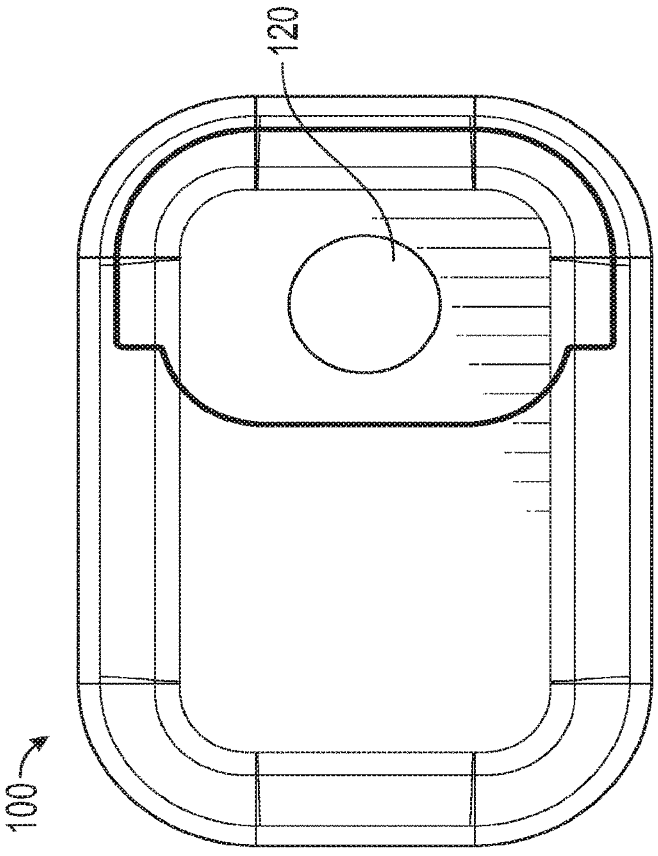
FIG. 10A shows a top view of a wearable sensor assembly according to another embodiment.

FIG. 10A shows a top view of the wearable sensor assembly 100.

Figure 10B:
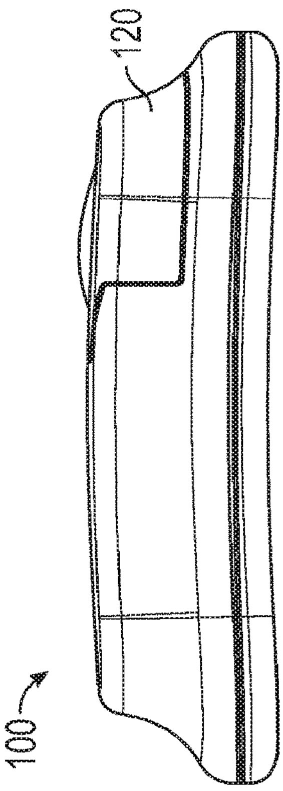
FIG. 10B shows a side view of the wearable sensor assembly of FIG. 10A.

FIG. 10B shows a side view of the wearable sensor assembly 100.

FIG. 10C shows a perspective view of the wearable sensor assembly 100.

Figure 11B:
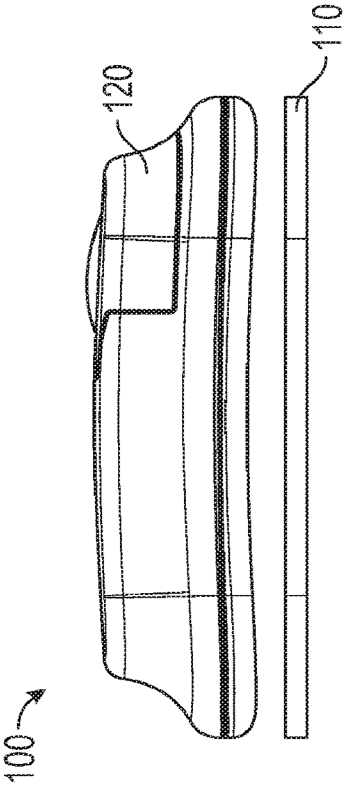
FIG. 11B shows a side view of the wearable sensor assembly of FIG. 11A.
Figure 11D:
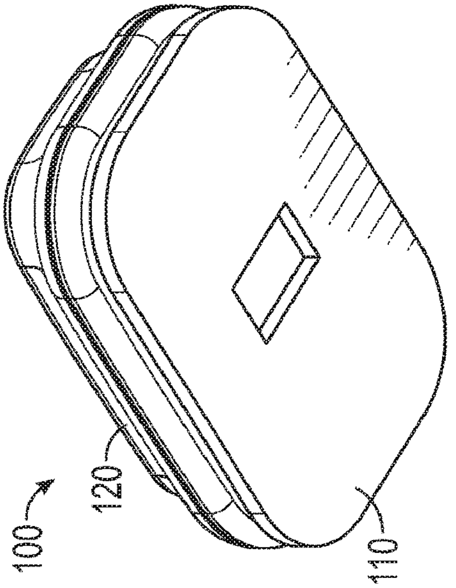
FIG. 11D shows a bottom perspective view of the wearable sensor assembly of FIG. 11A.
Figure 11A:
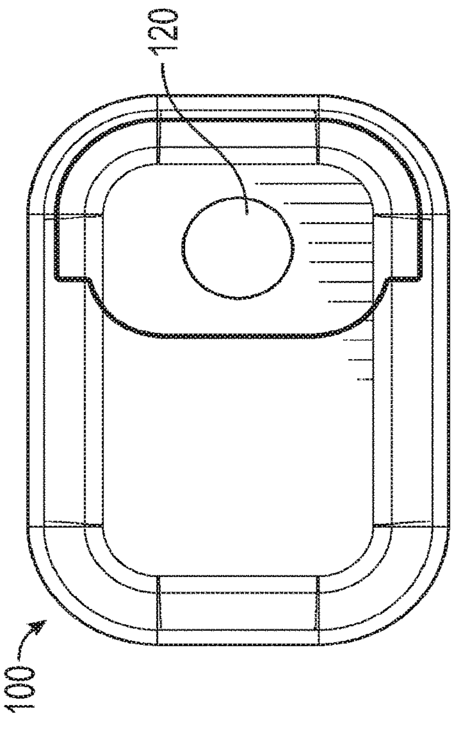
FIG. 11A shows a top view of a wearable sensor assembly.

FIG. 11A shows a top view of the wearable sensor assembly 100.

FIG. 11B shows a side view of the wearable sensor assembly 100.

Figure 11C:
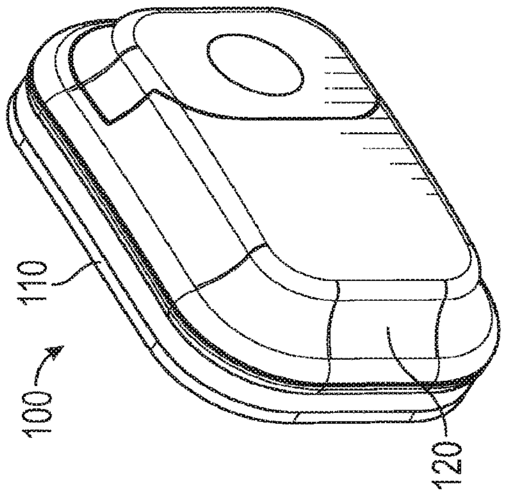
FIG. 11C shows a top perspective view of the wearable sensor assembly of FIG. 11A.

FIG. 11C shows a perspective view of the top of wearable sensor assembly 100.

FIG. 11D shows a perspective view of the bottom of wearable sensor assembly 100.

Figure 12:
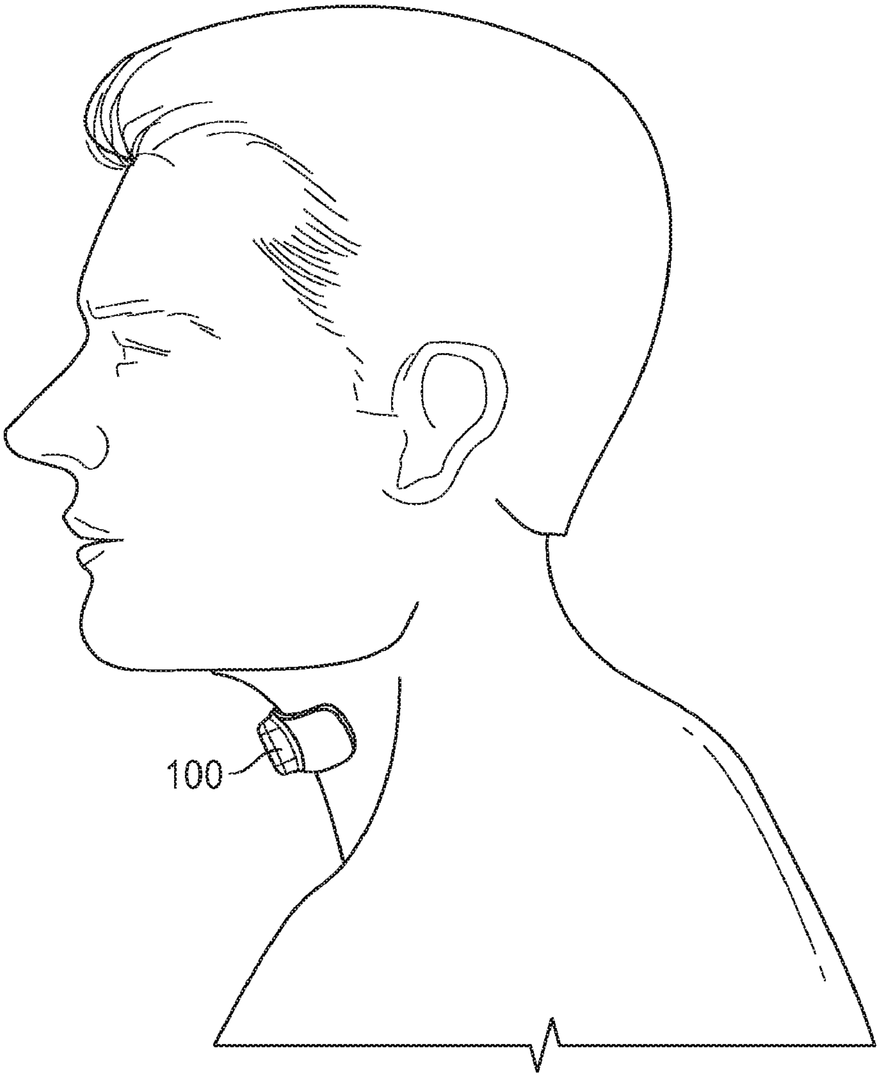
FIG. 12 shows a wearable sensor assembly positioned on the neck of a user.

FIG. 12 shows the wearable sensor assembly 100 positioned on the neck of a user. In this position on the front of the user's neck, the sensor can obtain signals for pulse oximetry, pulse, position, movement, snoring (auditory and vibrational signals), respiratory effort and respiratory flow movement.

Figure 13:
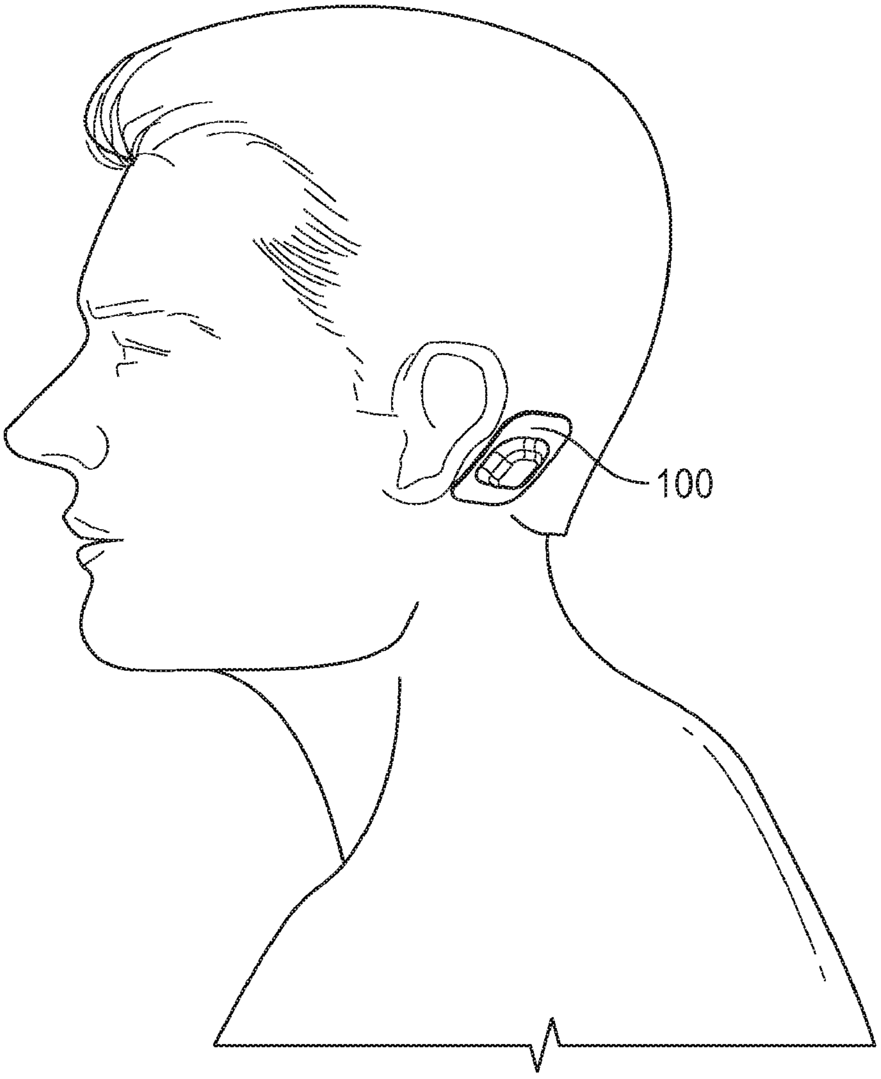
FIG. 13 shows a wearable sensor assembly positioned behind the ear of a user.

FIG. 13 shows the wearable sensor assembly 100 positioned behind the ear of a user. In this position over the bone behind the user's ear, the sensor can obtain signals for pulse oximetry, pulse, position, movement, snoring—both auditory and vibrational signals, respiratory effort and respiratory flow movement. This position is out of the way for the user and should not interfere with normal sleep habits. Additionally, this location is less visible.

Figure 14:
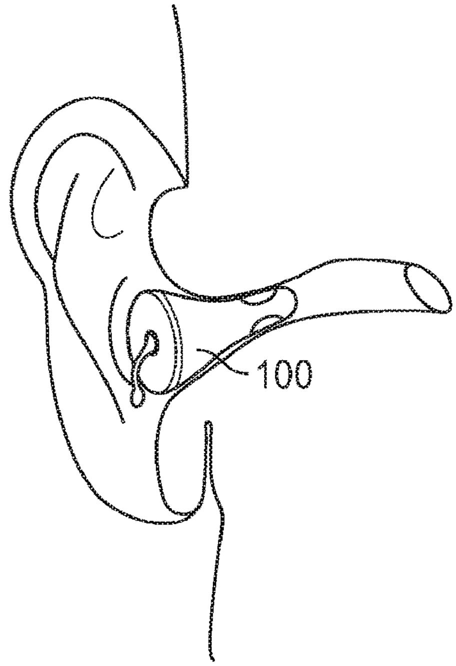
FIG. 14 shows a wearable sensor assembly positioned inside the ear canal of a user.

FIG. 14 shows the wearable sensor assembly 100 positioned inside the ear canal of a user. In this position the sensor can obtain signals for pulse oximetry, pulse, position, movement, snoring—both auditory and vibrational signals, and respiratory effort. This position is out of the way for the user and should not interfere with normal sleep habits. Additionally, this location is less visible.

Figure 15:
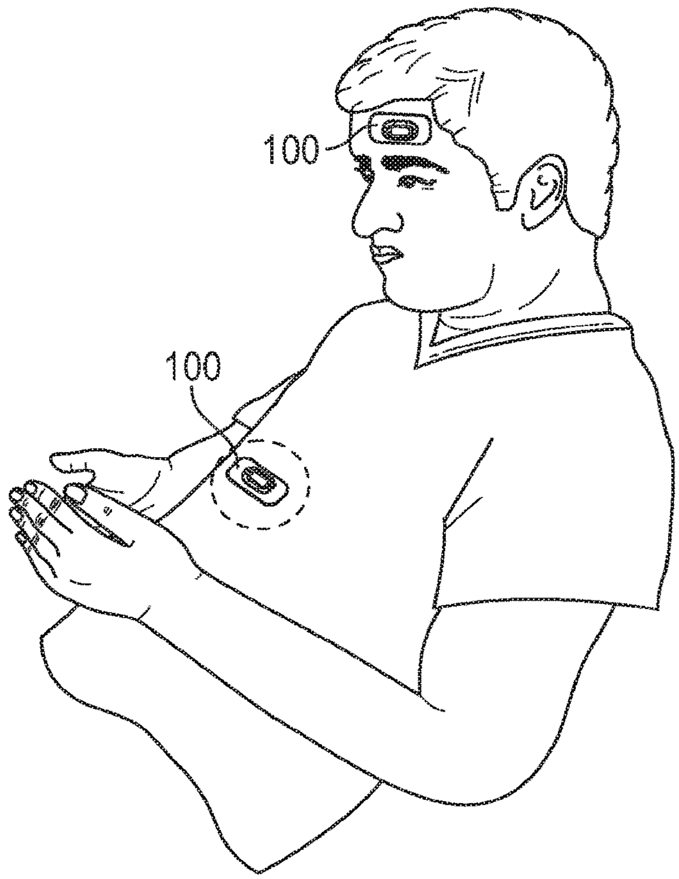
FIG. 15 shows a wearable sensor assembly in two different locations: the forehead and either the chest, belly, or torso.

FIG. 15 shows the wearable sensor assembly 100 in two different locations. One location is on the forehead. Another location is on the chest, belly, or torso. This can be achieved with two sensors worn simultaneously, or with one sensor worn in each location on different nights. The advantages of the forehead placement are discussed elsewhere. The chest placement offers several additional advantages. The motion of the chest during sleep yields a distinct motion signature from the sensor. This signal can be used to determine respiratory effort. Specifically, this is useful in differentiating Obstructive Sleep Apnea from Central or Mixed Sleep Apnea. Central Sleep Apnea is characterized by the absence of respiratory effort. Therefore, if a user has shown evidence of apnea with previous testing, using the sensor placed on the chest can determine if there are corresponding pauses in respiratory effort. By comparing the results from a sensor placed on the forehead to those from a sensor placed on the chest, it can be determined if Central Sleep Apnea is responsible. In some cases, this signal differentiation will be strong enough to indicate a diagnosis. In some cases, the signal differentiation may only be strong enough to indicate that further testing is justified to definitively diagnose the user. Central sleep apnea (CSA) is a neurologic disease in which breathing stops during sleep even though the airway is open. Both OSA and CSA disrupt sleep and carry significant long-term health consequences. These disorders require different therapies, and thus it is important for a diagnostic test to distinguish them.

Figure 16A:
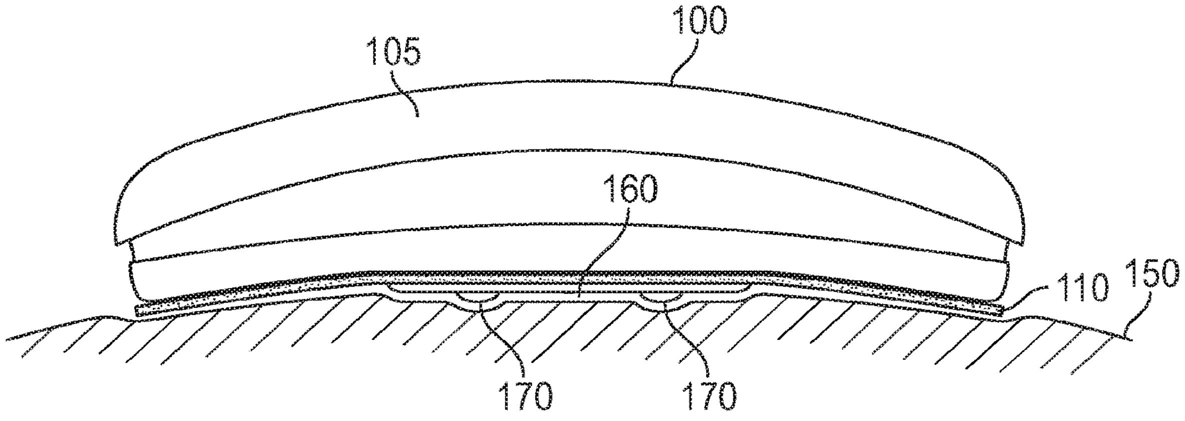
FIG. 16A shows a side view of a sensor according to another embodiment in place on a user's skin.
Figure 16B:
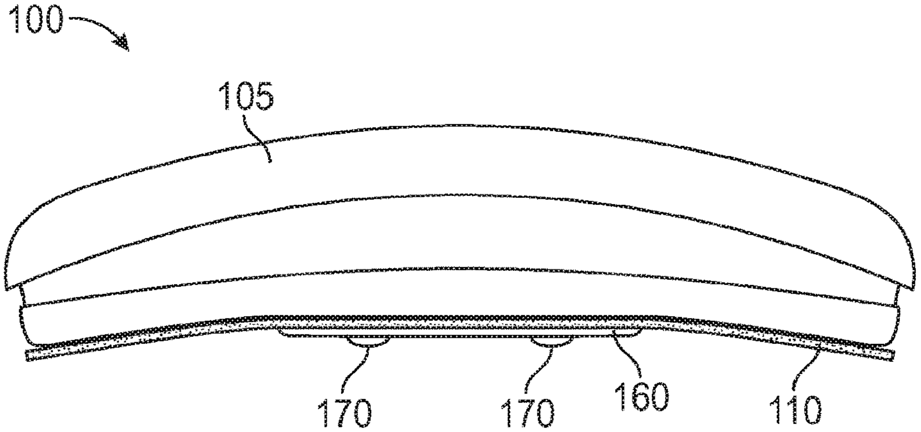
FIG. 16B shows a side view of the sensor of FIG. 16A.

FIG. 16A shows an embodiment of the wearable sensor assembly 100 in side view placed onto the skin tissue 150. The sensor interface element 160 extends downward from a peripheral portion of the housing 105 to form an optical engagement surface to directly couple the optical elements 170 with the skin tissue 150. This direct coupling helps ensure a quality raw optical signal is captured by the photodetector. FIG. 16B shows a side view of the wearable sensor assembly 100 of this embodiment. The manner in which the optical coupling elements 170 protrude into the surface of the skin, beyond the surface of the flexible skin attachment element 110, is shown. A typical distance for this is approximately 0.5 mm, with a typical range of 0.25 mm to 0.75 mm. However, this distance may vary to be as small at 0.1 mm or as large as 2.5 mm or larger. The elements must contact the skin sufficiently to produce the desired optical coupling and without an air gap for the optimal optical signal. However, if the elements protrude too far into the skin, they can significantly decrease blood perfusion and result in a poorer photoplethysmography signal. The optimal distance, as described herein, is needed to result in a favorable signal. The optical coupling elements 170 are comprised of optically-clear materials. To successfully optically couple the optical components with the skin, it is important that any air gaps are eliminated. Thus, a material that can eliminate air gaps and is optically clear fits two of the key parameters. One such material used in the instant invention is a 2 part epoxy. This material can flow during manufacturing to eliminate air gaps and is optically clear upon hardening.

Figure 17:
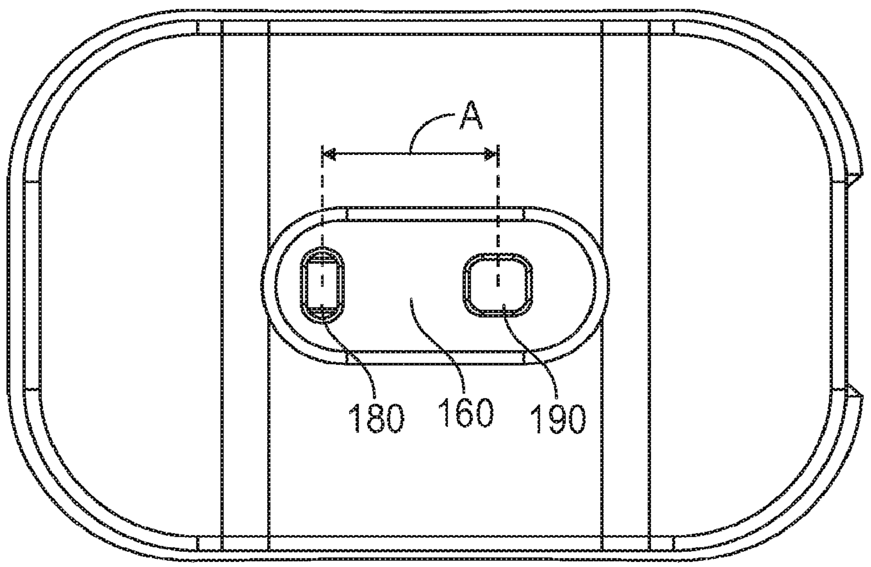
FIG. 17 shows a bottom view of the sensor of FIGS. 16A-B.

FIG. 17 shows an underside view of another embodiment of a wearable sensor assembly TOO, the side that is in contact with the skin tissue. Of note is the optical engagement surface of the sensor interface element 160, which engages the tissue. Within this element is the light source 180 and the photodetector 190. As is well known in pulse oximetry, the light source 180 may emit light at two different wavelengths (e.g., red light and infrared light), and the photodetector 190 may detect the time-based changes in absorption of the two light wavelengths to be used in a calculation of the user's blood oxygen saturation. A key dimension is the noted by A, the distance from the center of the energy emitting element 180 to the center of the energy detecting element 190. In one embodiment, this dimension A is 7 mm. In other embodiments, it can range from 5 mm-10 mm and yield a quality signal. It is important to be far apart enough so that the light energy emitted from the light source 180 must travel through enough blood-perfused tissue, including pulsatile blood, to result in a signal with enough time-variable, or AC, component to allow for an accurate blood oxygen saturation measurement. The emitting and detecting elements should be close enough together so that the detected time-variable signal is primarily composed of light energy from the emitter and not any other sources.

Figure 18A:
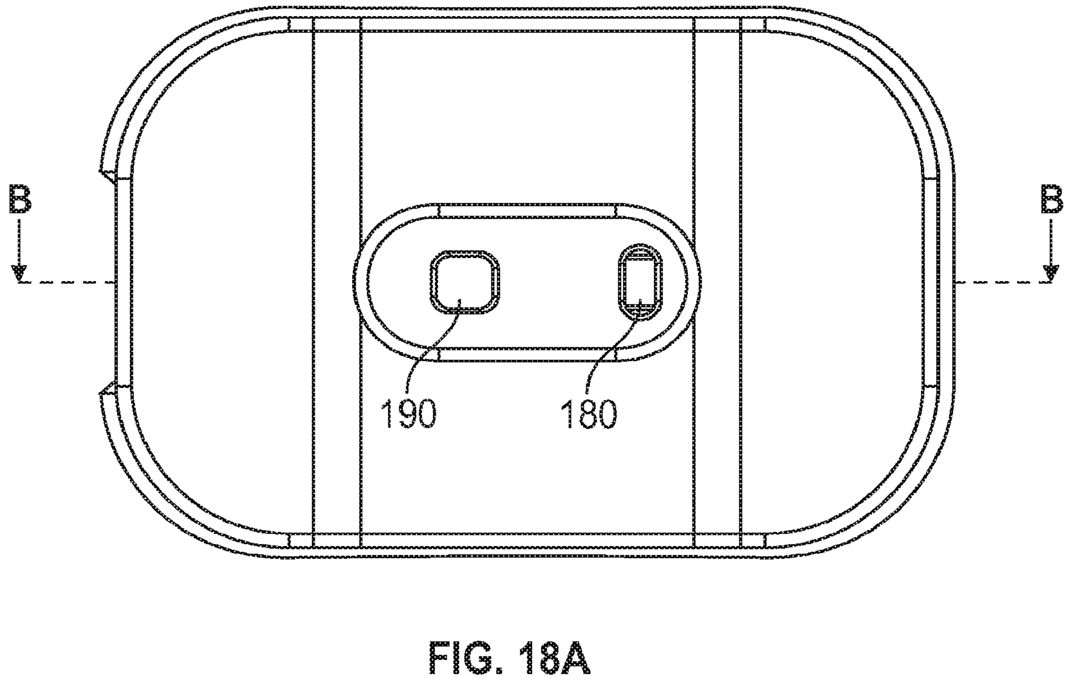
FIG. 18A is another bottom view of the sensor with additional dimensions.
Figure 18B:
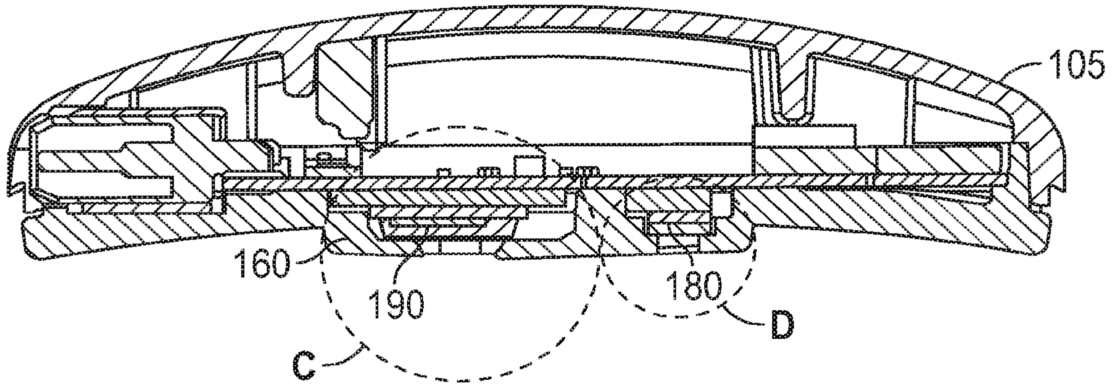
FIG. 18B shows a midline cut side view of the sensor.

FIGS. 18A and 18B show an underside view and a side view, respectively, of one embodiment of the wearable sensor assembly 100. The optical engagement surface of the raised sensor interface element 160 performs at least two key functions. One, it helps optically couple the device's optical components with the skin, as discussed herein. Second, it is also constructed of a light-blocking material specifically chosen to not allow passage of the wavelengths of interest emitted by the device. Some possible materials include thermoset and elastomeric materials which absorb the wavelengths of interest, including but certainly by no means limited to: ABS, polycarbonate, Santoprene™ thermoplastic, butyl styrene, and others. The wavelengths of interest are typically nominal 670 nm, 850 nm, and 900 nm.

FIG. 18B shows a side view of one embodiment of the wearable sensor assembly taken along the line B-B in FIG. 18A. Key components within the assembly include the photodetector element, the energy emitting element, the accelerometer, the wireless communication component, the microprocessor, and the battery. Also shown is the charging port, herein pictured as a USB connector in FIG. 18A. The adhesive flexible skin attachment element has been omitted from the figure for clarity. The microprocessor controls the function of the device. Energy is emitted from the energy emitting element into the tissue. In a preferred embodiment, the emitted energy is light in two distinct wavelengths of approximately 650 nm and 930 nm. Other wavelengths are possible, with one being in the red spectrum and the other in the infrared spectrum. This light passes through the tissue and then a portion of it is received by the photodetector. The photodetector receives the light energy and outputs a corresponding voltage to the strength of the intensity corresponding to each wavelength. From this data, the PPG waveform is determined, and the SpO2 is calculated. The PPG is the graph of the AC component of the intensity of these received signals over time. The SpO2 is calculated by: for a given time t, calculating 11Ared=(Redt−Redt−1)/((Redt+Redt−1)/2) and 11AIR=(IRt−IRt−1)/((IRt+IRt−1)/2); then graph 11Ared vs 11AIR, the slope of the best fit line is then R. The R value is then adjusted by coefficients to yield the SpO2, for instance using: (x)R2+(y)R+z=SpO2. In one embodiment, the SpO2 is calculated by the microprocessor on the device. In another embodiment, the raw signal data from the photodetector and accelerometer is sent by the wireless communication component to another device or service for processing. In yet another embodiment, the raw signal data undergoes preprocessing prior to being sent by the wireless communication component to another device or service for further processing.

Figure 18C:
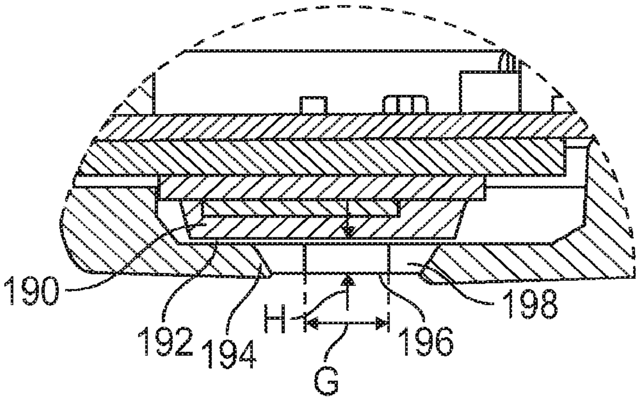
FIG. 18C shows a detail cutaway side view of the photodetector.

FIG. 18C shows a detailed side view (marked "C" in FIG. 18B) showing the photodetector 190 in the housing 105. Of note is a tapered frustoconical surface 194 extending from the photodetector 190 and tapering down to an opening 196 in the housing. This downward taper angle is important to allow the maximum amount of light signal to reach the sensor. In one embodiment, the angle of the taper is 45 degrees, although it can range from 5-85 degrees. The dimension G denotes the diameter of the opening of the aperture. In one embodiment, this dimension G is slightly smaller than the active surface 192 of the photodetector 190. FIG. 18C also shows a dimension H, the distance from the surface 192 of the photodetector 190 to the opening 196 in the housing. In one embodiment, this distance is minimized to allow for the optimal signal to pass through. Optically clear material 198 is disposed in the volume extending between the opening 196 and the active surface 192 of the photodetector 190. Other device components supported within the housing include a position sensor (e.g., accelerometer), a controller and a communicator (e.g., wireless transmitter.

Figure 18D:
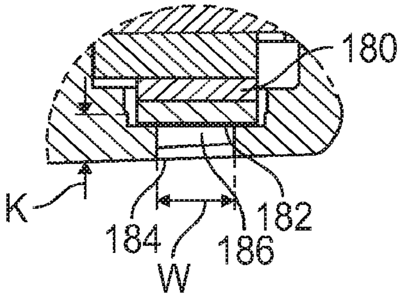
FIG. 18D shows a detail cutaway side view of the emitter element.

FIG. 18D shows a detailed cutaway side view of the light source 180. In one embodiment, the W dimension, which describes the light source opening 184 in the housing, is sized to be smaller than the active area 182 of light source 180. Dimension K shows the distance from the surface of the energy emitting element to the exterior surface of the housing. In one embodiment, this distance is minimized to allow for an optimal amount of light to pass through. Optically clear material 186 is disposed in the volume extending between the opening 184 and the active area 182 of the light source 180. In one embodiment, the light source is a pair of light emitting diodes (LED). In one embodiment, these LEDs operate in the wavelengths of approximately 650 nm and approximately 930 nm. Many other wavelengths are possible. Some specific wavelengths found to work well are 656-657 nm and 930-932 nm.

Figure 19:
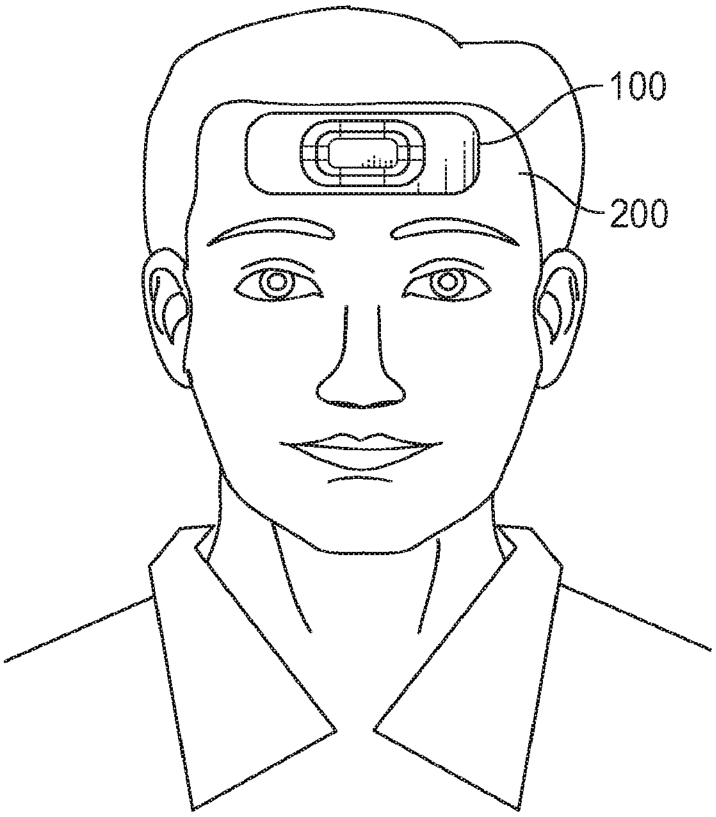
FIG. 19 shows placement of the sensor on the user's forehead.

FIG. 19 shows a placement zone of the device 100 for on the forehead 200 of the user according to one embodiment of the invention. While it is possible to get adequate readings anywhere on the forehead, placing the device 100 in the upper half of the forehead results in significantly better signal quality. The zone illustrated in FIG. 19 is above and between both eyes, and the upper half of the forehead as defined by the area between the eyebrows and the hairline. This area is characterized by more microvasculature and smaller vessels which typically result in a better perfusion signal. This yields a larger AC component of the PPG waveform, allowing for more detail to be derived from the signal. The readings taken from this zone can often be doubly strong, with twice the perfusion index, as readings taken from the lower half of the forehead. This upper half zone is preferred for the most accurate signal results.

Figure 20A:
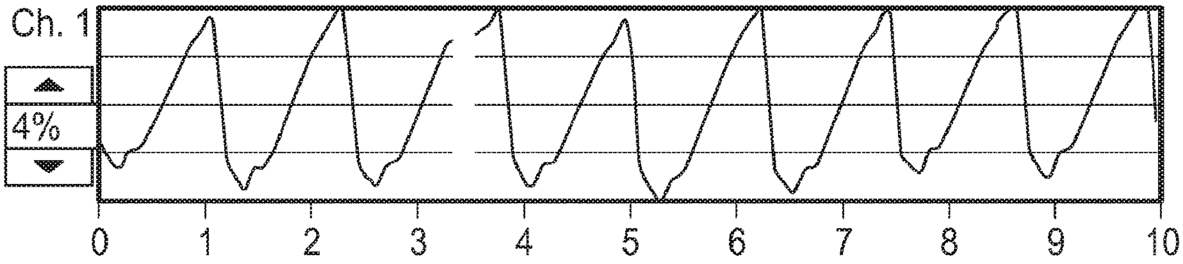
FIG. 20A shows a raw PPG signal from a supine positioned subject.
Figure 20B:
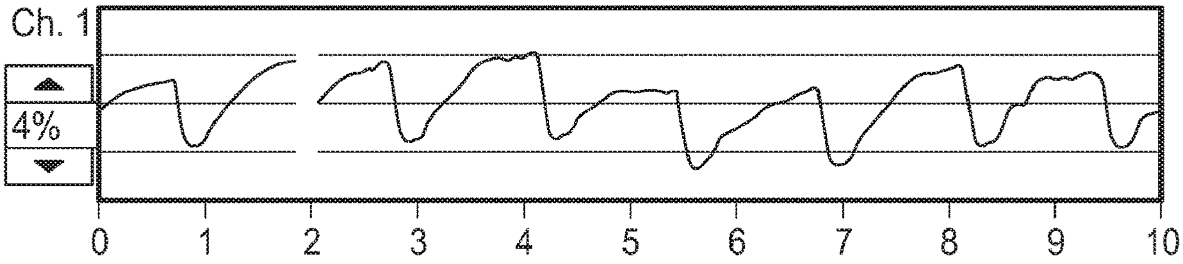
FIG. 20B shows a raw PPG signal from a left lateral positioned subject.
Figure 20C:
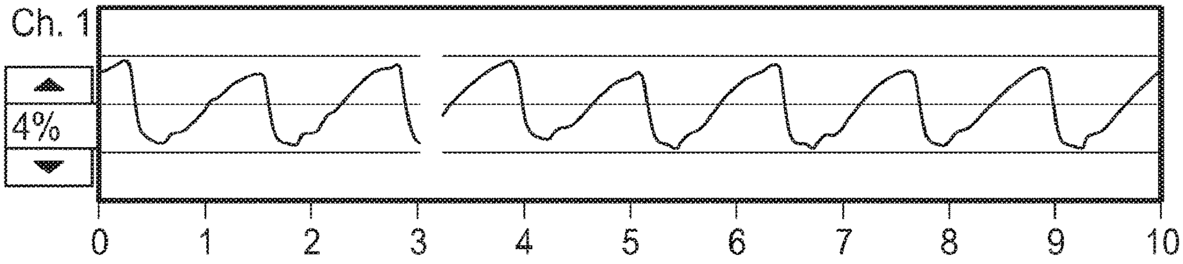
FIG. 20C shows a raw PPG signal from a right lateral positioned subject.

FIG. 20A shows a portion of the PPG signal taken from a subject in the supine position. The amplitude of the signal indicates the perfusion index, the ratio of the pulsatile bloodflow to the non-pulsatile blood. The signal also shows a characteristic shape with relatively narrow peaks. In contrast, the waveforms shown in FIG. 20B and FIG. 20C show a lower amplitude and perfusion index that is about one-half that of FIG. 20A. Additionally, the waveform in FIG. 20B is flattened on top and shows a distinctly different shape than that of FIG. 20A. Likewise, the waveform in FIG. 20C is also more rounded on top and shows a distinctly different shape than that of FIG. 20A. These changes in the waveform and the perfusion index can be used to determine the position of the sleeper. First, the PPG waveforms are characterized in each of the supine and non-supine cases, which allows threshold levels to be determined for each case. These threshold levels are used to compare to a given PPG waveform to output a position determination of the sleeper. In another embodiment, the waveforms for supine and non-supine sleep are compared using digital signal processing techniques to characterize the shape of each waveform. This is used to determine thresholds for waveform shape, which are then applied to a given PPG waveform to determine the user's position.

Another advantage of the system and methods described herein is the ability to identify other oxygen-related illnesses and conditions. Such conditions include altitude illness, lung diseases, COPD, emphysema, bronchitis, pulmonary edema, fibrosis, pneumonia, congenital defects, congestive heart failure, anemia, narcotics use, anesthetics use, and certain poisonings like cyanide.

What is claimed is:

1. A device for obstructive sleep apnea detection comprising:

a housing having a sensor interface element comprising an optical engagement surface adapted to engage skin of a user;

a position sensor disposed in the housing and adapted to obtain position data that indicates whether the user is in a first patient sleeping position or a second patient sleeping position;

a first optical element disposed in the housing and adapted to emit light through a first opening in the optical engagement surface;

a second optical element disposed in the housing adapted to receive the light through a second opening in the optical engagement surface, the second optical element configured to:

generate a first detected light signal associated with first position data that indicates the first patient sleeping position and a second detected light signal associated with second position data that indicates the second patient sleeping position, wherein the first detected light signal corresponds to a first plurality of blood oxygen saturation events occurring when the user is in the first patient sleeping position and the second detected light signal corresponds to a second plurality of blood oxygen saturation events occurring when the user is in the second patient sleeping position; and a controller adapted to:

obtain one or more analysis results for the first patient sleeping position and the second patient sleeping position based at least in part on comparing a frequency of the first plurality of blood oxygen saturation events occurring when the user is in the first patient sleeping position with a frequency of the second plurality of blood oxygen saturation events occurring when the user is in the second patient sleeping position and an average value of the first plurality of blood oxygen saturation events occurring when the user is in the first patient sleeping position with an average value of the second plurality of blood oxygen saturation events occurring when the user is in the second patient sleeping position, wherein a blood oxygen saturation event occurs when a detected light signal satisfies a threshold value; and record in memory the one or more analysis results for the first patient sleeping position and the second patient sleeping position in accordance with the comparison.

2. The device of claim 1, further comprising:

a flexible material disposed below the housing and around the sensor interface element.

3. The device of claim 2, further comprising:

a first optical coupling element disposed in the first opening below the first optical element and a second optical coupling element disposed in the second opening below the second optical element.

4. The device of claim 2, wherein the flexible material is configured to conform to anatomy of the user.

5. The device of claim 1, wherein a diameter of the second opening is smaller than a diameter of an active surface of the second optical element.

6. The device of claim 1, further comprising:

a communicator adapted to communicate the one or more analysis results for the first patient sleeping position and the second patient sleeping position.

7. The device of claim 6, wherein the communicator is configured to:

provide feedback to the user based at least in part on displaying the one or more analysis results for the first patient sleeping position and the second patient sleeping position.

8. The device of claim 6, wherein the communicator comprises a wireless transmitter disposed in the housing.

9. The device of claim 1, wherein the first optical element and the second optical element comprise an optically-clear material.

10. The device of claim 1, wherein the optical engagement surface comprises material preferentially absorbing one or more light wavelengths emitted by the first optical element.

11. The device of claim 1, wherein the position sensor comprises an accelerometer.

12. The device of claim 1, wherein the position sensor is adapted to determine the first patient sleeping position from the first detected light signal and the second patient sleeping position from the second detected light signal.

13. The device of claim 1, wherein the one or more analysis results are obtained over a plurality of nights.

14. A method for obstructive sleep apnea detection comprising:

obtaining position data that indicates whether a user is in a first patient sleeping position or a second patient sleeping position;

generating, at one or more optical elements, a first detected light signal associated with first position data that indicates the first patient sleeping position and a second detected light signal associated with second position data that indicates the second patient sleeping position, wherein the first detected light signal comprises a first plurality of blood oxygen saturation events occurring when the user is in the first patient sleeping position and the second detected light signal comprises a second plurality of blood oxygen saturation events occurring when the user is in the second patient sleeping position;

obtaining one or more analysis results for the first patient sleeping position and the second patient sleeping position based at least in part on comparing a frequency of the first plurality of blood oxygen saturation events occurring when the user is in the first patient sleeping position with a frequency of the second plurality of blood oxygen saturation events occurring when the user is in the second patient sleeping position and an average value of the first plurality of blood oxygen saturation events occurring when the user is in the first patient sleeping position with an average value of the second plurality of blood oxygen saturation events occurring when the user is in the first patient sleeping position, wherein a blood oxygen saturation event occurs when a detected light signal satisfies a threshold value; and recording in memory the one or more analysis results for the first patient sleeping position and the second patient sleeping position in accordance with the comparison.

15. The method of claim 14, further comprising:

communicating the one or more analysis results for the first patient sleeping position and the second patient sleeping position.

16. The method of claim 15, further comprising:

providing feedback to the user based at least in part on displaying the one or more analysis results for the first patient sleeping position and the second patient sleeping position.

17. The method of claim 14, wherein the one or more optical elements comprise an optically-clear material.

18. The method of claim 14, further comprising:

determining the first patient sleeping position and the second patient sleeping position from an accelerometer.

19. The method of claim 14, further comprising:

determining the first patient sleeping position from the first detected light signal and the second patient sleeping position from the second detected light signal.

20. The method of claim 14, wherein the one or more analysis results are obtained over a plurality of nights.

* * * * *